US012629183B2

(12) United States Patent
Segina et al.

(10) Patent No.: US 12,629,183 B2
(45) Date of Patent: May 19, 2026

(54) CANNULATED REDUCTION PIN AND ALIGNING DEVICE

(71) Applicant: Genesis Medical Devices LLC, Indialantic, FL (US)

(72) Inventors: Daniel Nick Segina, Satellite Beach, FL (US); James A. Proctor, Jr., Indialantic, FL (US)

(73) Assignee: Genesis Medical Devices LLC, Indialantic, FL (US)

( * ) Notice: Subject to any disclaimer, the term of this patent is extended or adjusted under 35 U.S.C. 154(b) by 0 days.

(21) Appl. No.: 18/420,896

(22) Filed: Jan. 24, 2024

(65) Prior Publication Data

US 2024/0285320 A1      Aug. 29, 2024

Related U.S. Application Data

(63) Continuation of application No. 18/296,662, filed on Apr. 6, 2023, now Pat. No. 12,232,786, which is a continuation of application No. 17/223,130, filed on Apr. 6, 2021, now Pat. No. 11,633,217.

(60) Provisional application No. 63/006,397, filed on Apr. 7, 2020.

(51) Int. Cl.
| | |
|---|---|
| *A61B 17/72* | (2006.01) |
| *A61B 17/17* | (2006.01) |
| *A61B 17/66* | (2006.01) |
| *A61B 17/68* | (2006.01) |
| *A61B 17/80* | (2006.01) |
| *A61B 17/84* | (2006.01) |

(52) U.S. Cl.
CPC ...... *A61B 17/7291* (2013.01); *A61B 17/8052* (2013.01); *A61B 17/842* (2013.01); *A61B 17/1728* (2013.01); *A61B 17/1775* (2016.11);

*A61B 17/66* (2013.01); *A61B 2017/681* (2013.01); *A61B 17/8061* (2013.01); *A61B 17/808* (2013.01); *A61B 17/848* (2013.01)

(58) Field of Classification Search
CPC ............ A61B 17/7291; A61B 17/8061; A61B 17/1728; A61B 17/1775; A61B 17/66; A61B 17/8052; A61B 17/808; A61B 17/842; A61B 17/848; A61B 17/86; A61B 2017/681
USPC ......... 606/286, 62, 280, 281, 300, 86 R, 87, 606/96–99, 104, 86 B, 902, 915
See application file for complete search history.

(56) References Cited

U.S. PATENT DOCUMENTS

| | | | | | |
|---|---|---|---|---|---|
| 4,978,349 | A | * | 12/1990 | Frigg ................... | A61B 17/744 |
| | | | | | 606/62 |
| 2006/0069324 | A1 | * | 3/2006 | Block ................. | A61B 17/864 |
| | | | | | 600/595 |
| 2015/0173904 | A1 | * | 6/2015 | Stark ................... | A61F 2/30988 |
| | | | | | 623/18.11 |
| 2017/0119436 | A1 | * | 5/2017 | Farzadfard ............. | A61B 17/66 |

OTHER PUBLICATIONS

Paragon28. Calc Fracture Plating System, Paragon28, Inc, Englewood, Co, 2017, https://paragon28.com/app/uploads/2016/03/P51-STG-0006-RevA.pdf. Accessed Jul. 31, 2024 (Year: 2017).*

* cited by examiner

*Primary Examiner* — Marcela I. Shirsat
(74) *Attorney, Agent, or Firm* — David Thibodeau, Jr.; VLP Law Group LLP

(57) ABSTRACT

A cannulated Shantz pin for use with a fracture fixation apparatus and method.

6 Claims, 26 Drawing Sheets

1A-100

2A-20

2A-10

PF

CF

PT 2A-30

5A-10

5A-20

5A-30

5A-50

5A-40

5A-60

5A-75

5A-70

5A-90

5A-80

8A-10

8A-20

8A-30

8A-105

8A-100

12A-50

12A-105

12A-100

14A-145

14A-100

14A-140

15A-60

15A-100    15A-150    15A-140

1C-10

1C-20

3C-10

3C-30

3C-40

CF

PF 3C-60

P T 3C-50

CANNULATED REDUCTION PIN AND ALIGNING DEVICE

CROSS-REFERENCE TO RELATED APPLICATIONS

This application claims priority to a co-pending U.S. patent application Ser. No. 18/296,662 filed Apr. 6, 2023 entitled "Reduction and Fixation Apparatus for Calcaneal Fracture" and also to a co-pending U.S. patent application Ser. No. 17/223,130 filed Apr. 6, 2021 entitled "Reduction and Fixation Apparatus for Calcaneal Fracture" which in turn claims priority to U.S. Provisional Patent Application Ser. No. 63/006,397 filed Apr. 7, 2020 entitled "Reduction and Fixation Apparatus for Calcaneal Fracture", the entire contents of each of which are hereby incorporated by reference.

BACKGROUND OF THE INVENTION

This application relates to reduction and fixation of fractures such as calcaneal fractures.

SUMMARY OF THE INVENTION

As described herein, preferred embodiments for a fracture fixation apparatus and/or method may include a cannulated pin for acting on a bone fragment. The cannulated pin may be a Shantz pin having a threaded portion for interfacing with the bone fragment; a canulated center portion for accepting a wire; and a coupling interface portion.

The coupling interface portion provides for insertion and extraction of the Schantz pin; interfacing to a canulated manipulation handle, which also accepts the wire via a canulated portion of the manipulation handle, and aligning the cannulated portion of the manipulation handle with the cannulated center portion of the Schantz pin so as to allow an acceptance of the wire and insertion of the wire into the bone fragment.

The manipulation handle may be further usable for adjusting a position of the bone fragment relative to one or more other bones or other bone fragments prior to the insertion of the wire into the bone fragment.

The cannulated Schantz pin may be further configured for removal from the bone fragment following the insertion of the wire into the one or more other bones or other bone fragments while leavening the wire in place and allowing the wire to retain alignment during an exchange of the pin with a cannulated screw.

Other features and advantages will be evident from the detailed description that follows.

BRIEF DESCRIPTION OF THE DRAWINGS

At least one specification heading is required. Please delete this heading section if it is not applicable to your application. For more information regarding the headings of the specification, please see MPEP 608.01(a). Additional novel features and advantages of the approaches discussed herein are evident from the text that follows and the accompanying drawings, where.

DETAILED DESCRIPTION

Figure 1:
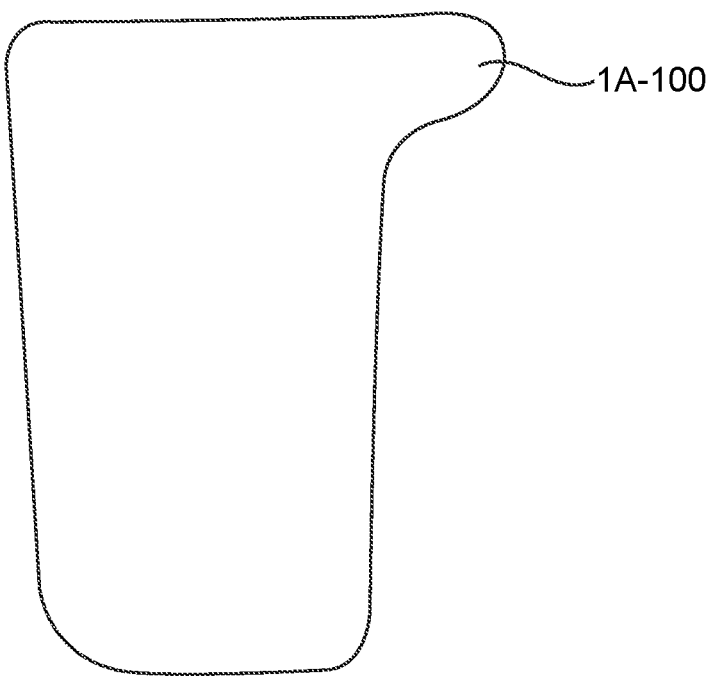
FIG. 1 is a depiction of a calcaneal bone in coronal cross-section.

FIG. 1 is a depiction of a calcaneal bone in coronal cross-section. Reference number 1A-100 indicates the outline of the bone through a portion anatomically described as the posterior facet/middle facet. Note this is only one depiction of the bone via a cross-sectional cut in the coronal plane.

US 12,629,183 B2

3

Figure 2:
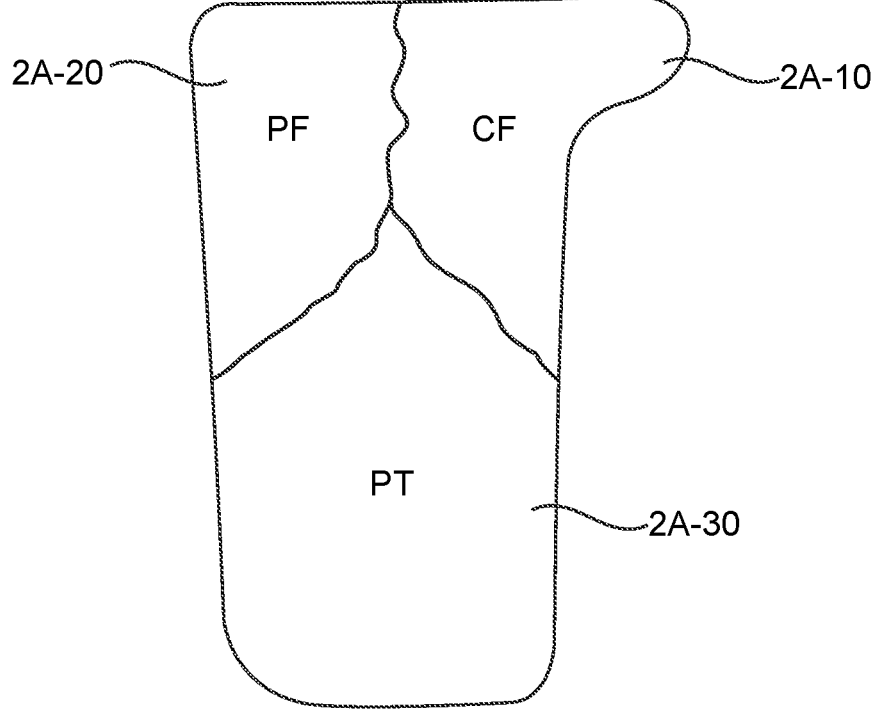
FIG. 2 is a depiction of the same coronal cross-section of the calcaneal bone with added features to depict a common fracture pattern through the joint surface.

FIG. 2 is a depiction of the same coronal cross-section of the calcaneal bone with added features to depict a common fracture pattern through the joint surface. The three main components of the fracture 2A-10 are depicted as the constant fragment/CF, 2A-20 the posterior facet/PF, and the 2A-30 the posterior tuberosity/PT.

Figure 3:
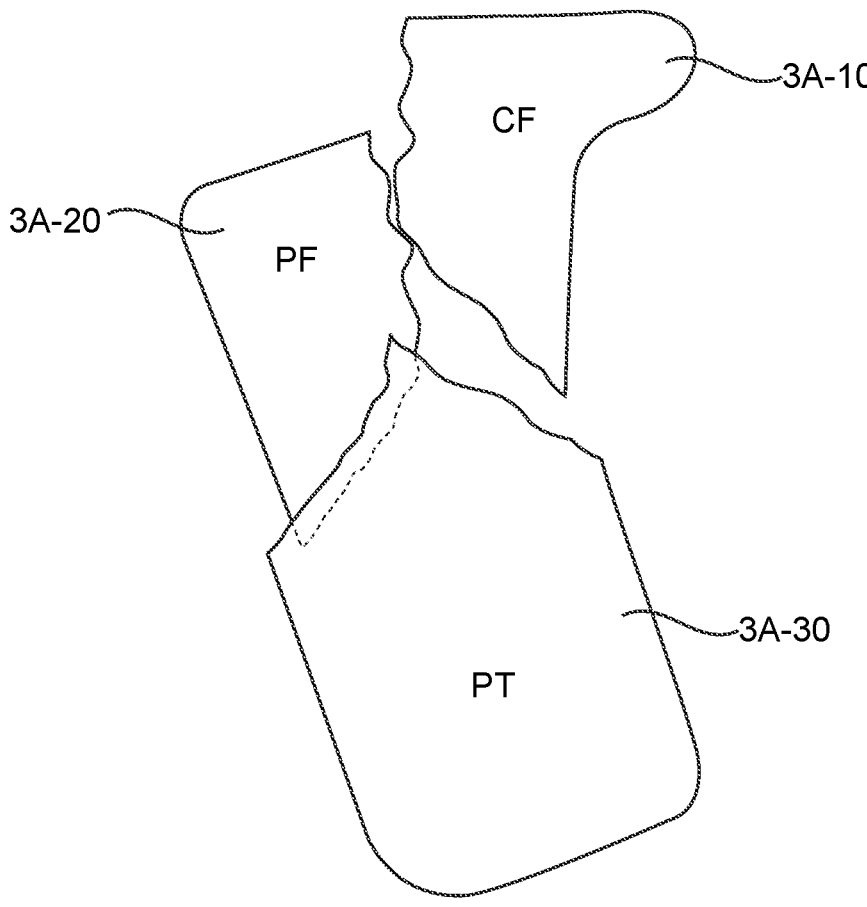
FIG. 3 is a depiction of a displaced fracture noting the three main components.

FIG. 3 is a depiction of a displaced fracture noting the three main components labeled as follows: 3A-10 the constant fragment, 3A-20 the posterior facet fragment, and 3A-30 the posterior tuberosity fragment of the fracture pattern.

Figure 4:
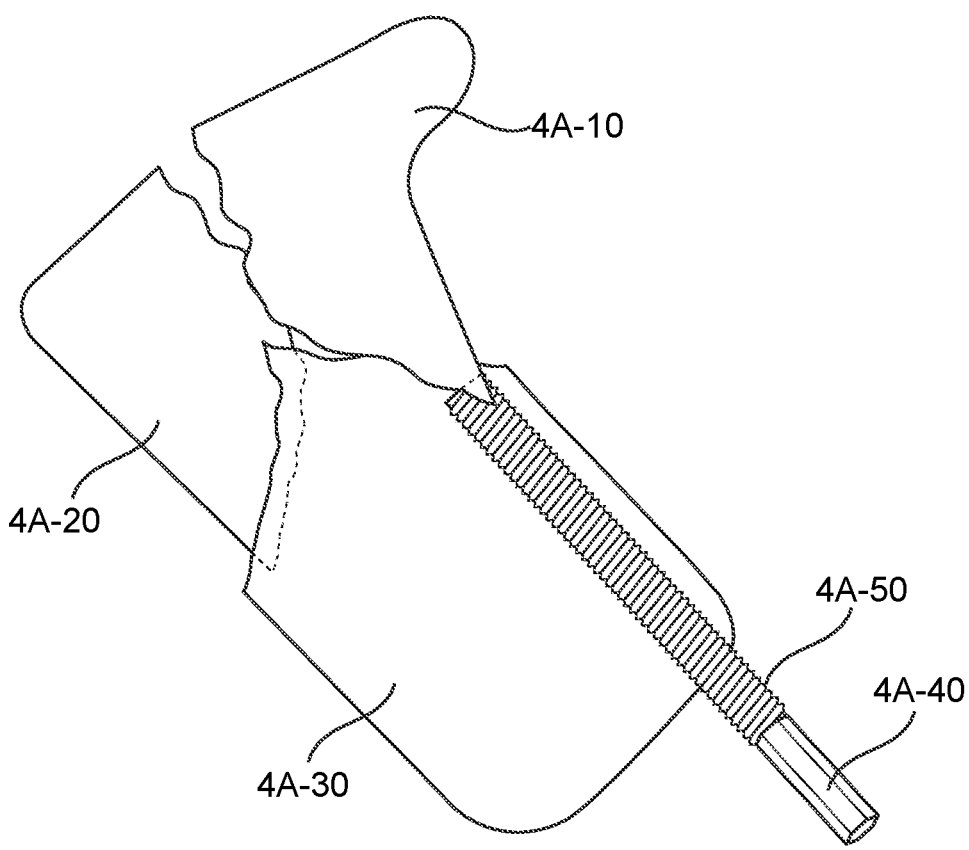
FIG. 4 is a depiction of an embodiment of the reduction tool of the present disclosure.

FIG. 4 is a depiction of an embodiment of the reduction tool of the present disclosure. The cannulated-threaded reduction tool component 4A-50 is inserted into the posterior tuberosity, 4A-30. The portion of the threaded reduction tool 4A-50 which protrudes outside the bone, 4A-30 is shown as 4A-40. The geometry of 4A-40 has multiple embodiments but is designed to accommodate additional exterior coupling component (ECC) which will be described and depicted in FIG. 5.

Figure 5:
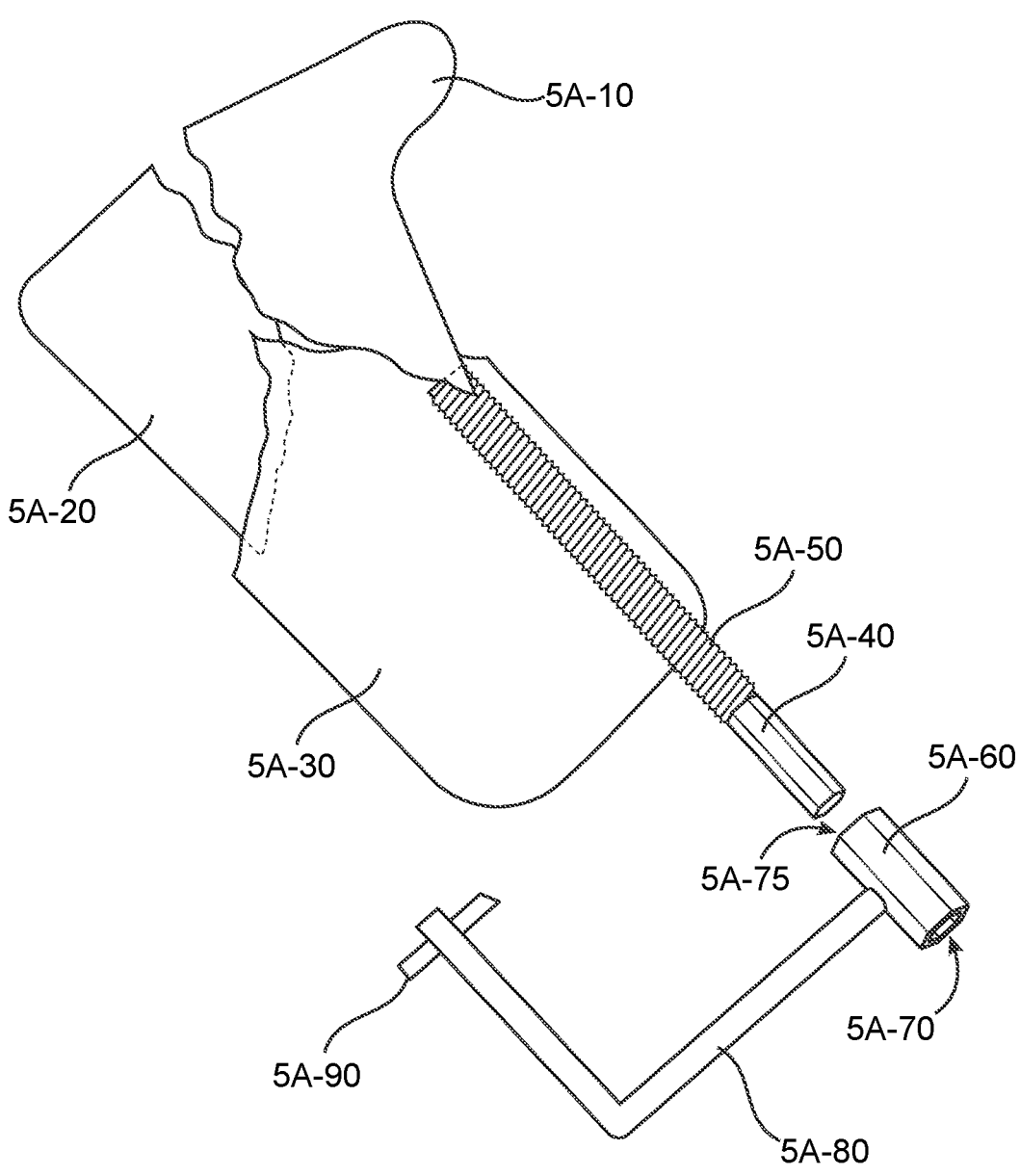
FIG. 5 is a depiction of an embodiment including an additional exterior coupling component (ECC) to the reduction tool.

FIG. 5 is a depiction of an embodiment including an additional exterior coupling component (ECC) to the reduction tool. The coupling takes place between the cannulated-threaded component of the tool, 5A-50 at the hexagonally depicted interface, 5A-40. The component space to allow for coupling is depicted as 5A-75. The exterior coupling component (ECC) comprised of 5A-60, 5A-70, 5A-80 and 5A-90 is designed to telescope over 5A 40 and has concomitantly matching the geometry to provide for coupling and rotational stability, in this embodiment. The hexagonally depicted interface, 5A-40 is elongated to protrude through 5A-60 to exit at 5A-70. The protruding arm of the exterior coupling component (ECC), 5A-80, is depicted to lie outside of the bone and skin of the posterior tuberosity, 5A-30. A coupling wire/stabilizing wire sleeve is depicted as 5A-90.

Figure 6:
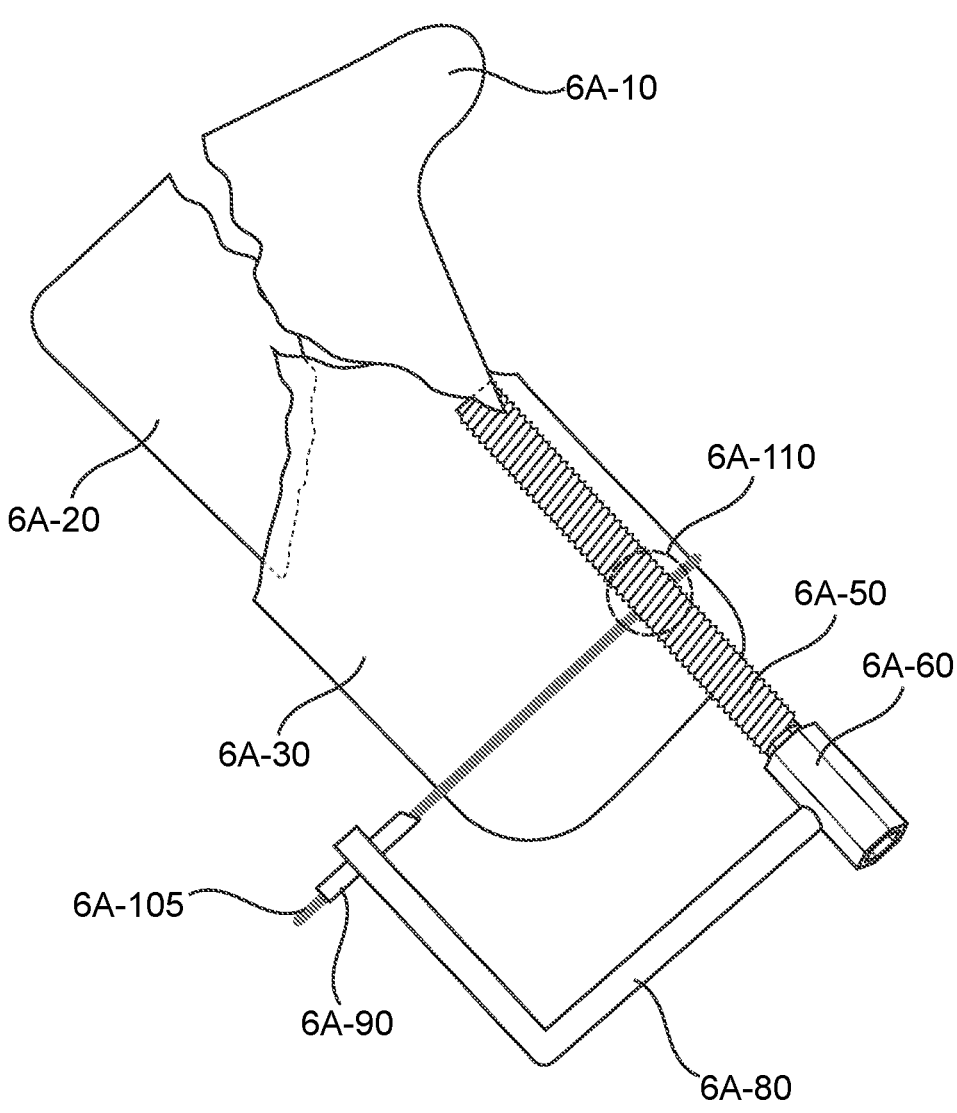
FIG. 6 is an embodiment depicting the insertion of a coupling wire/stabilizing wire

FIG. 6 is an example embodiment depicting the insertion of a coupling wire/stabilizing wire 6A-105 through a coupling wire/stabilizing wire sleeve 6A-90. The wire is inserted through the bone of the posterior facet depicted as 6A-30 to lie at a perpendicular orientation to the cannulated-threaded reduction component 6A-50, in this embodiment. The interface is shown as 6A-110. The embodiment depicting in FIG. 6 now demonstrates the coupling taking place between the cannulated-threaded reduction component 6A-50 and the hexagonal component of the outrigger depicted as 6A-60. Note that these two components, 6A-50 and 6A-60 are registered and locked into position now functioning as one unit. The combination of 6A-90, 6A-80, 6A-60, and 6A-50 collectively comprise this embodiment of the reduction too (also depicted in FIG. 7 as 7A-100).

Figure 7:
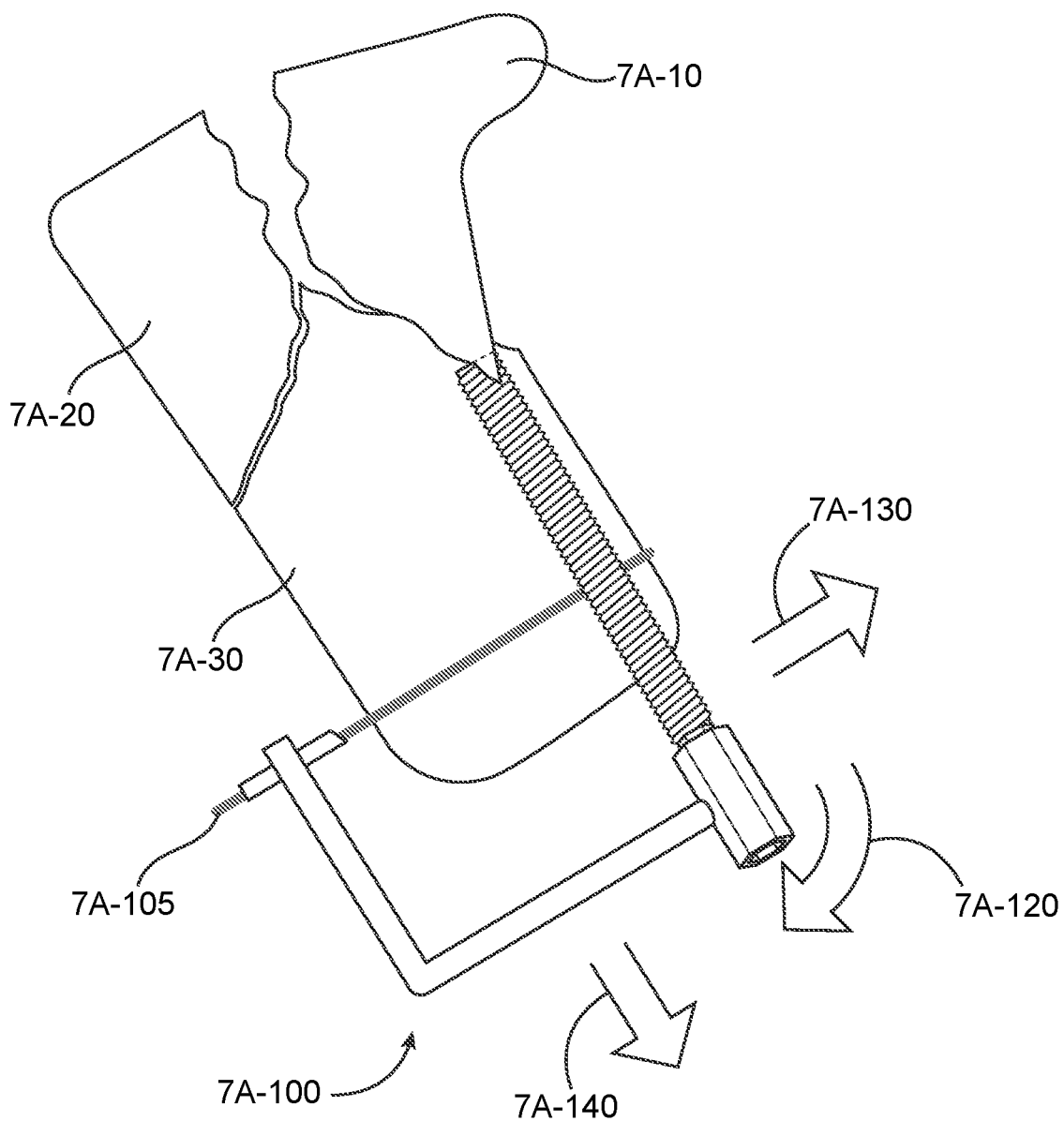
FIG. 7 depicts an embodiment of the assembled reduction tool

FIG. 7 depicts an embodiment of the assembled reduction tool 7A-100 and coupling wire/stabilizing wire 7A-105 seated within the posterior facet, 7A-30. Reduction maneuvers that are performed are now capable due to the capturing of the posterior facet, 7A-30. These maneuvers include medialization of the posterior facet, 7A-30 through the Vector 7A-130. Additionally, Varus angulation is corrected through the vector depicted as 7A-120. Finally, appropriate calcaneal height is restored via distraction depicted through the Vector 7A-140.

Figure 8:
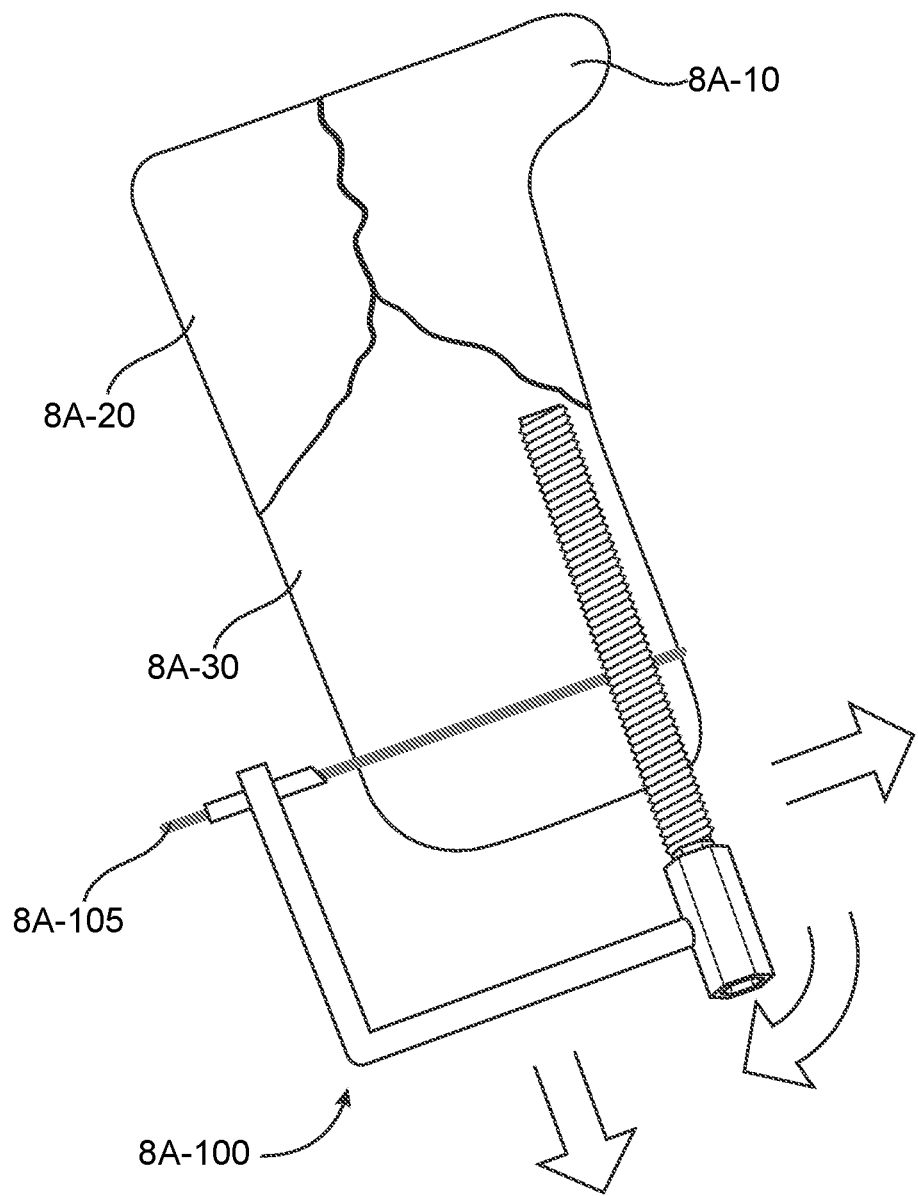
FIG. 8 depicts the reduced/restored anatomy of the calcaneus where the alignment between the constant fragment, the posterior facet fragment, and the posterior facet fragment are anatomically realigned.

FIG. 8 depicts the reduced/restored anatomy of the calcaneus where the alignment between the constant fragment, 8A-10, the posterior facet fragment, 8A-20 and the posterior facet fragment, 8A 30 are now anatomically realigned. An embodiment of the assembled reduction tool 8A-100 and coupling wire/stabilizing wire 8A-105 are also shown.

4

Figure 9:
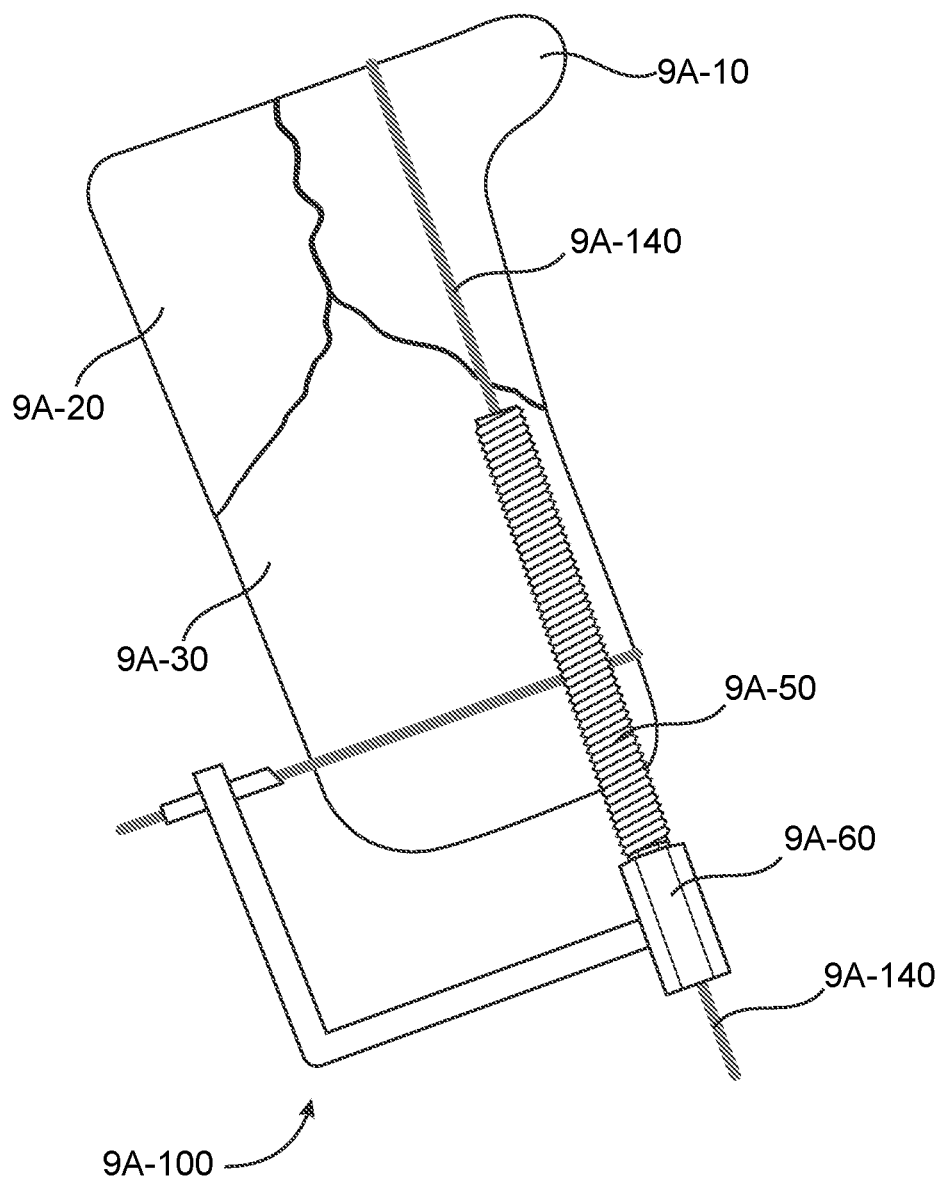
FIG. 9 depicts the restored anatomy between the constant fragment, the posterior facet fragment, and the posterior tuberosity component.

FIG. 9 depicts the restored anatomy between the constant fragment, 9A-10, the posterior facet fragment, 9A-20 and the posterior tuberosity component, 9A-30. An embodiment of the threaded anchoring/distraction wire 9A-140 can now be inserted through the threaded-cannulated portion (9A-50) of the reduction tool 9A-100, as well as a hexagonal outrigger 9A-60, into or around the CF fracture fragment 9A-10, in some embodiments. Additional orthogonal drawings will follow to further provide detail to the components of the reduction tool, is some embodiments.

Figure 10:
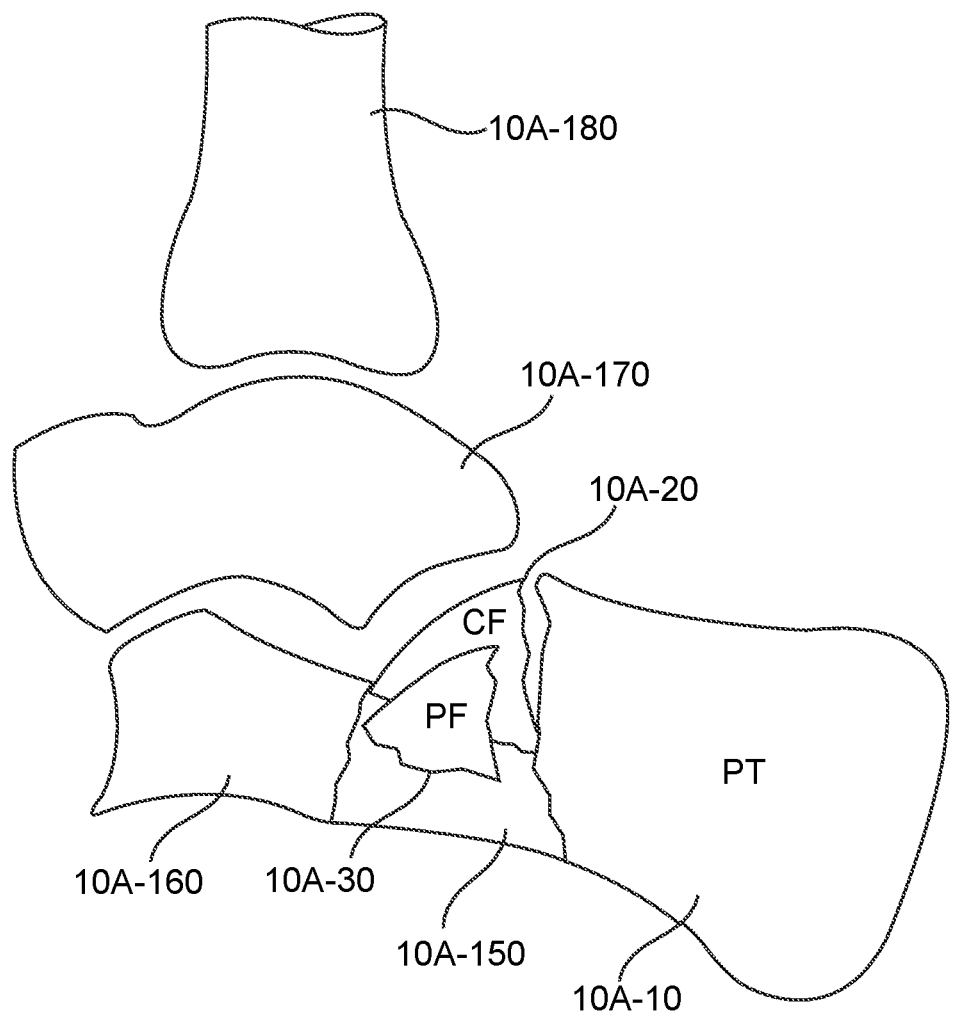
FIG. 10 depicts multiple bones in sagittal cross section including: the distal tibia, the talus and the calcaneus depicted in multiple fragments.

FIG. 10 depicts the multiple bones in sagittal cross section including: the distal tibia (10A-180), the talus (10A-170) and the calcaneus depicted in multiple fragments. This drawing is now done in perpendicular to previous FIG. 1, proving a sagittal view of the bones. Additional detailed components of the calcaneal fracture include the posterior tuberosity fragment (10A-10), the constant fragment (10A-20), the posterior facet fragment (10A-30) as well as additional fragments of the fracture now seen including the plantar cortex (10A-150) and the anterior process (10A-160).

Figure 11:
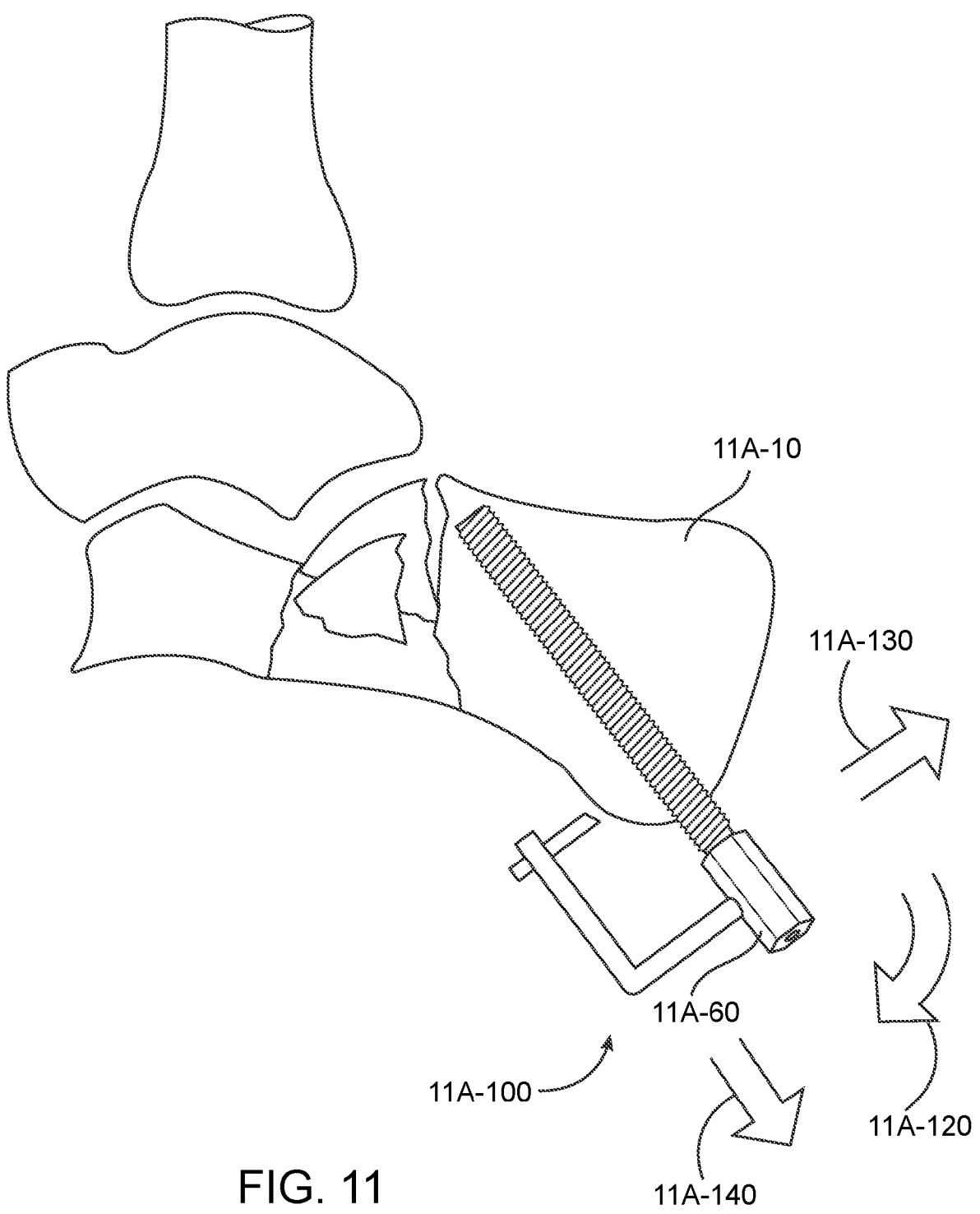
FIG. 11 depicts the orthogonal view to FIG. 4.

FIG. 11 depicts the orthogonal view to FIG. 4. This embodiment of the assembled reduction tool (11A-100) resides in the posterior tuberosity 11A-10 to provide for the reduction maneuvers, depicted as Vectors 11A-130, 11A-120 and 11A-140.

Figure 12:
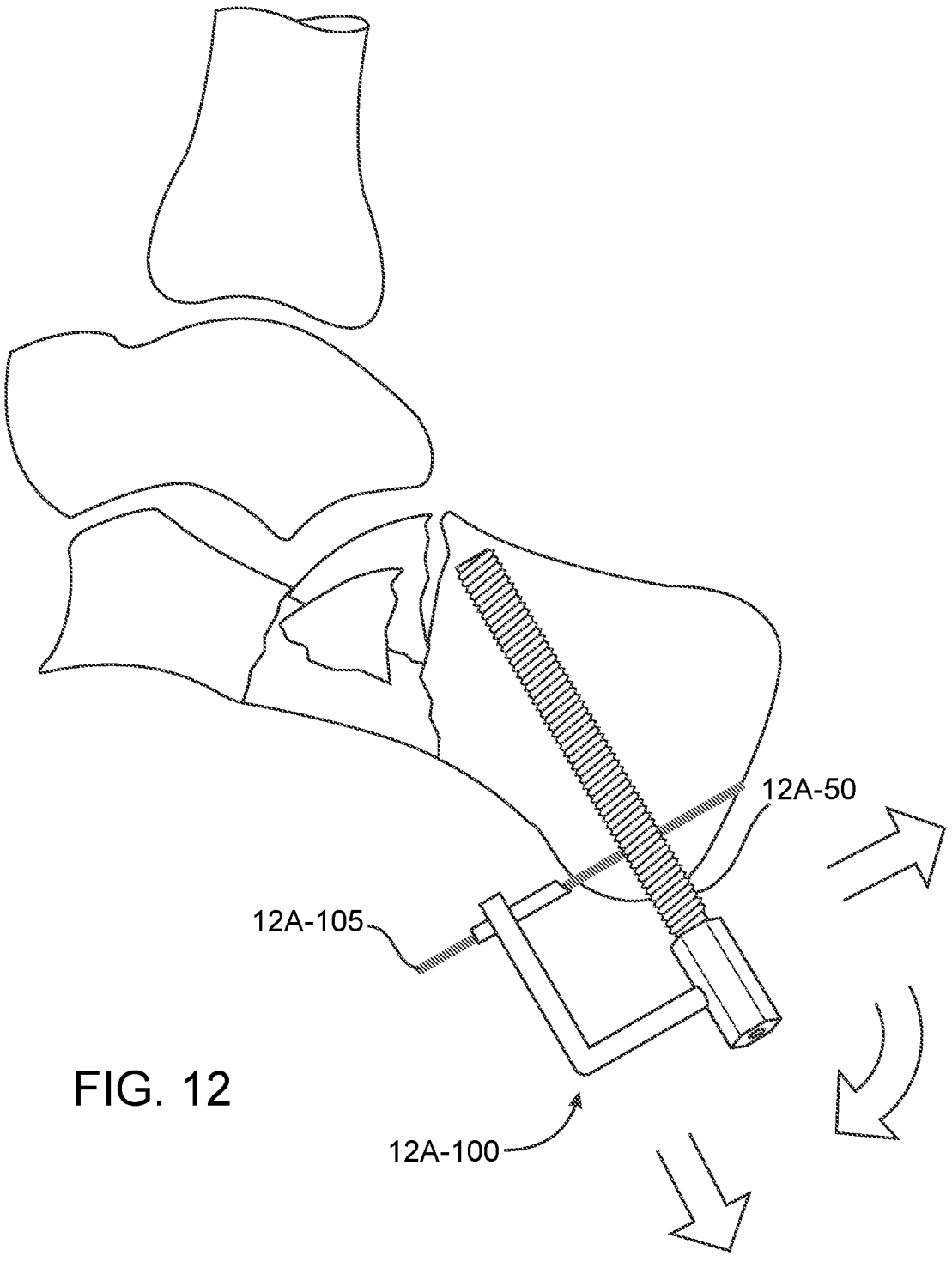
FIG. 12 provides additional detail of the anchoring wire placed through an embodiment of the assembled reduction tool.

FIG. 12 provides additional detail of the anchoring wire 12A-105 placed through an embodiment of the assembled reduction tool (12A-100) and inserted in a 90-degree orientation to the threaded cannulated reduction (12A-50) screw component of the assembled reduction tool (12A-100).

Figure 13:
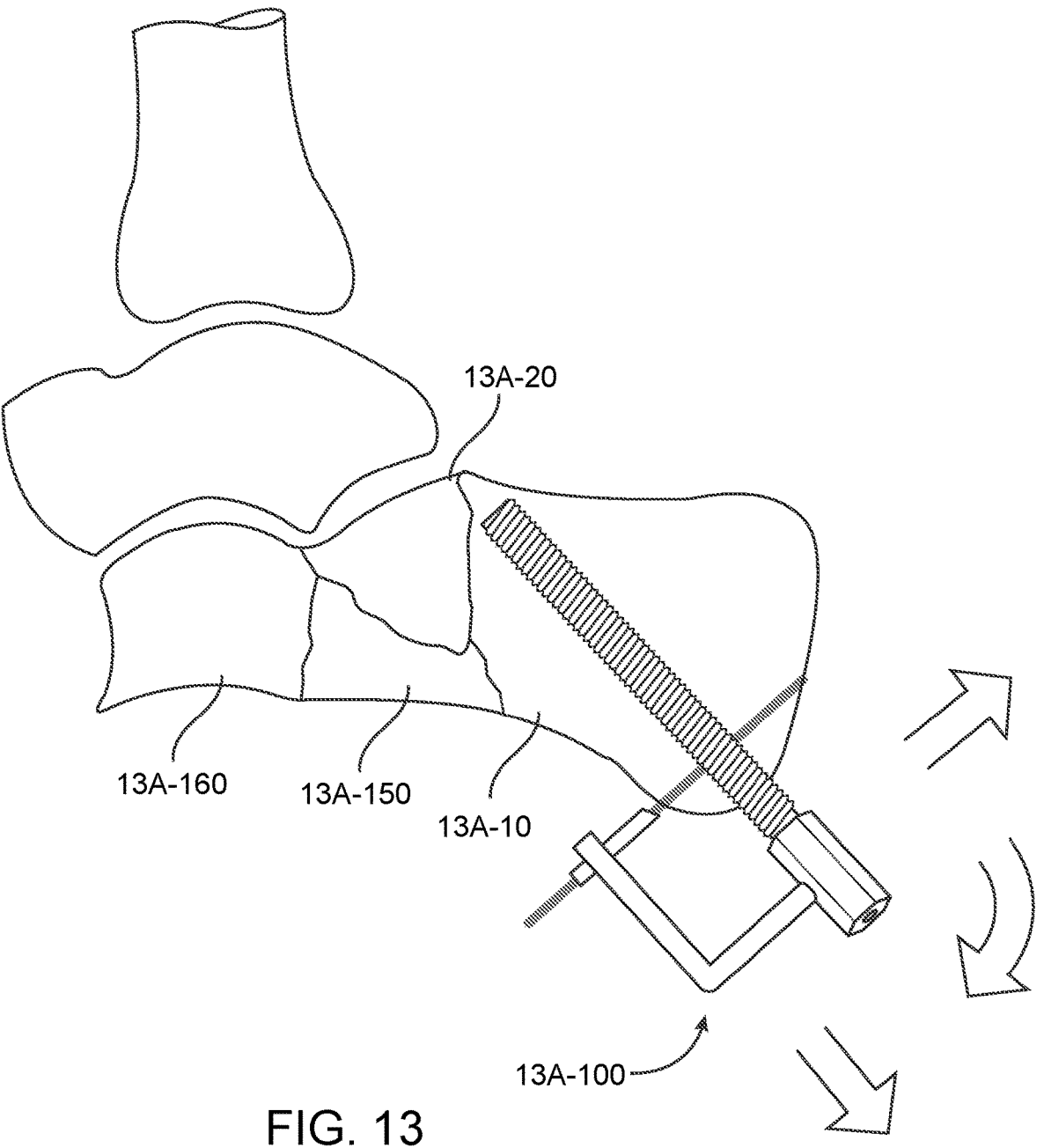
FIG. 13 depicts the restored anatomy of the calcaneus with the aid of an embodiment of the assembled reduction tool

FIG. 13 depicts the restored anatomy of the calcaneus with the aid of an embodiment of the assembled reduction tool (13A-100). The restored articular anatomy is depicted as 13A-20 with other components of the fracture drawn as the posterior tuberosity, 13A-10, the plantar cortex, 13A-150 as well as the anterior process, 13A-160.

Figure 14:
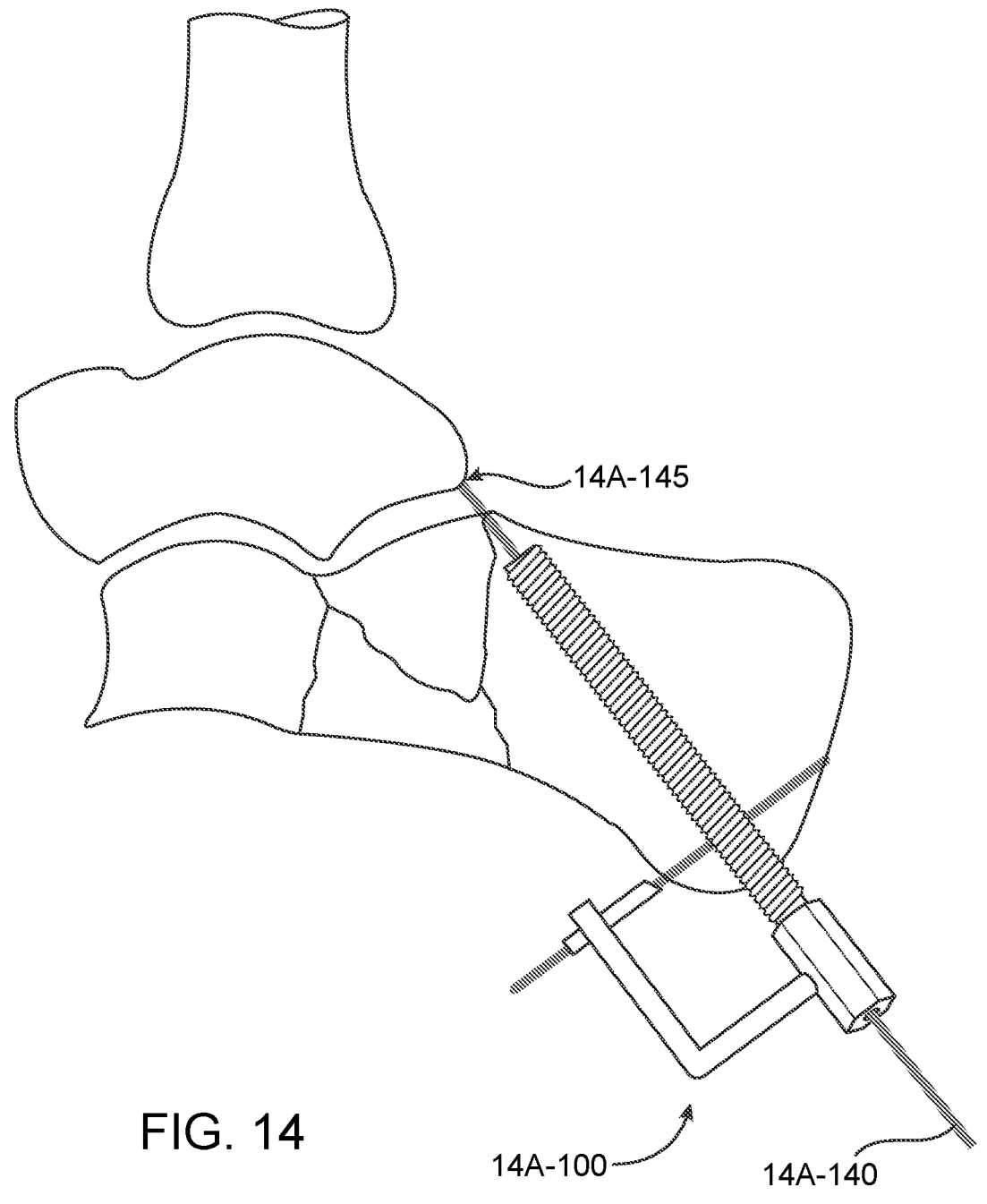
FIG. 14 depicts the insertion of an embodiment of the threaded distraction wire through the an embodiment of the assembled reduction tool.

FIG. 14 depicts the insertion of an embodiment of the threaded distraction wire, 14A-140, through an embodiment of the assembled reduction tool (14A-100) anchoring into the posterior portion of the talus at interface 14A-145.

Figure 15:
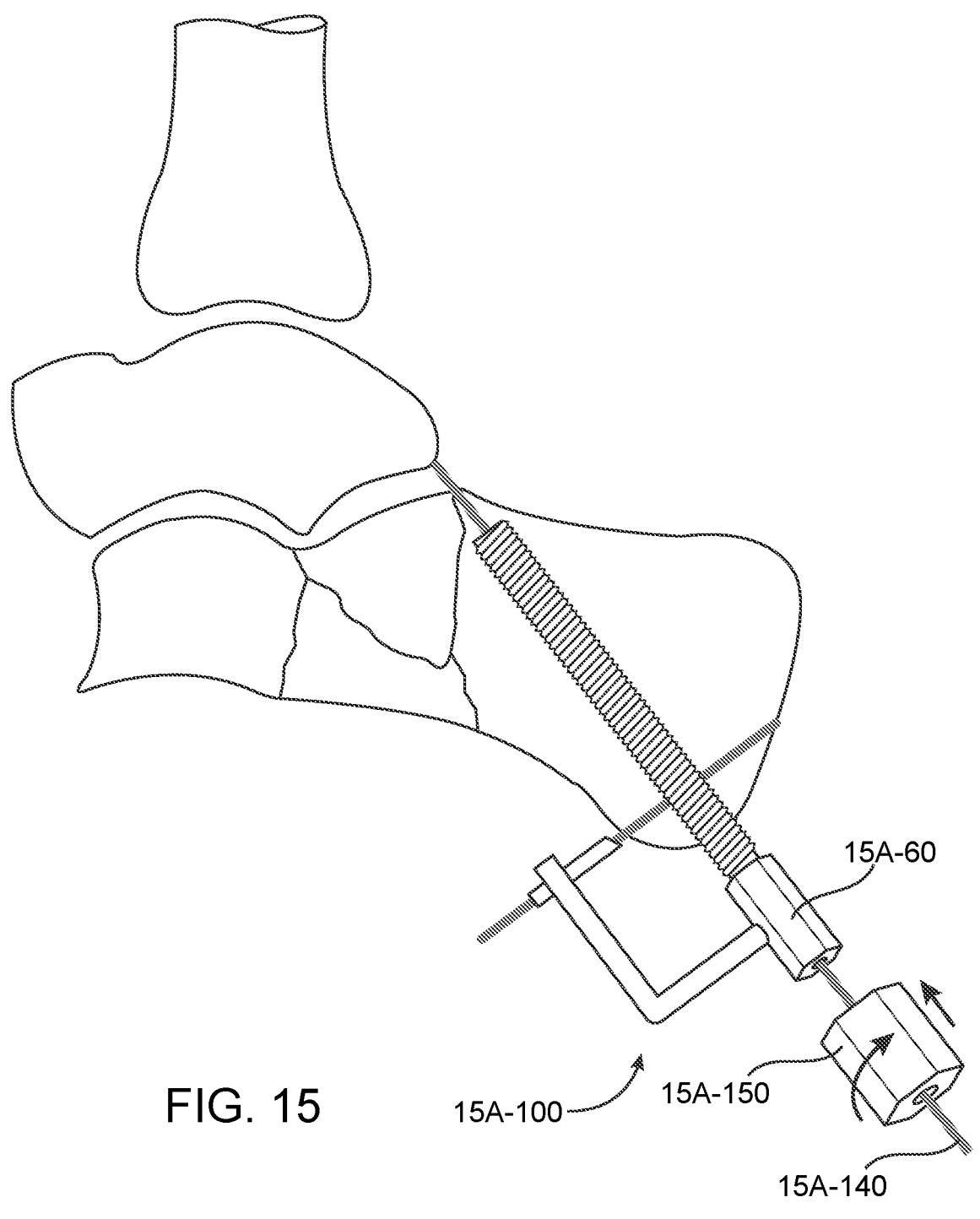
FIG. 15 depicts the placement of an embodiment of the distraction bolt/nut.

FIG. 15 depicts the placement of an embodiment of the distraction bolt/nut 15A-150. The nut is threaded to provide for advancement over the threaded distraction wire, 15A-140, as it couples to the component 15A-60 of the reduction tool 15A-100.

Figure 16:
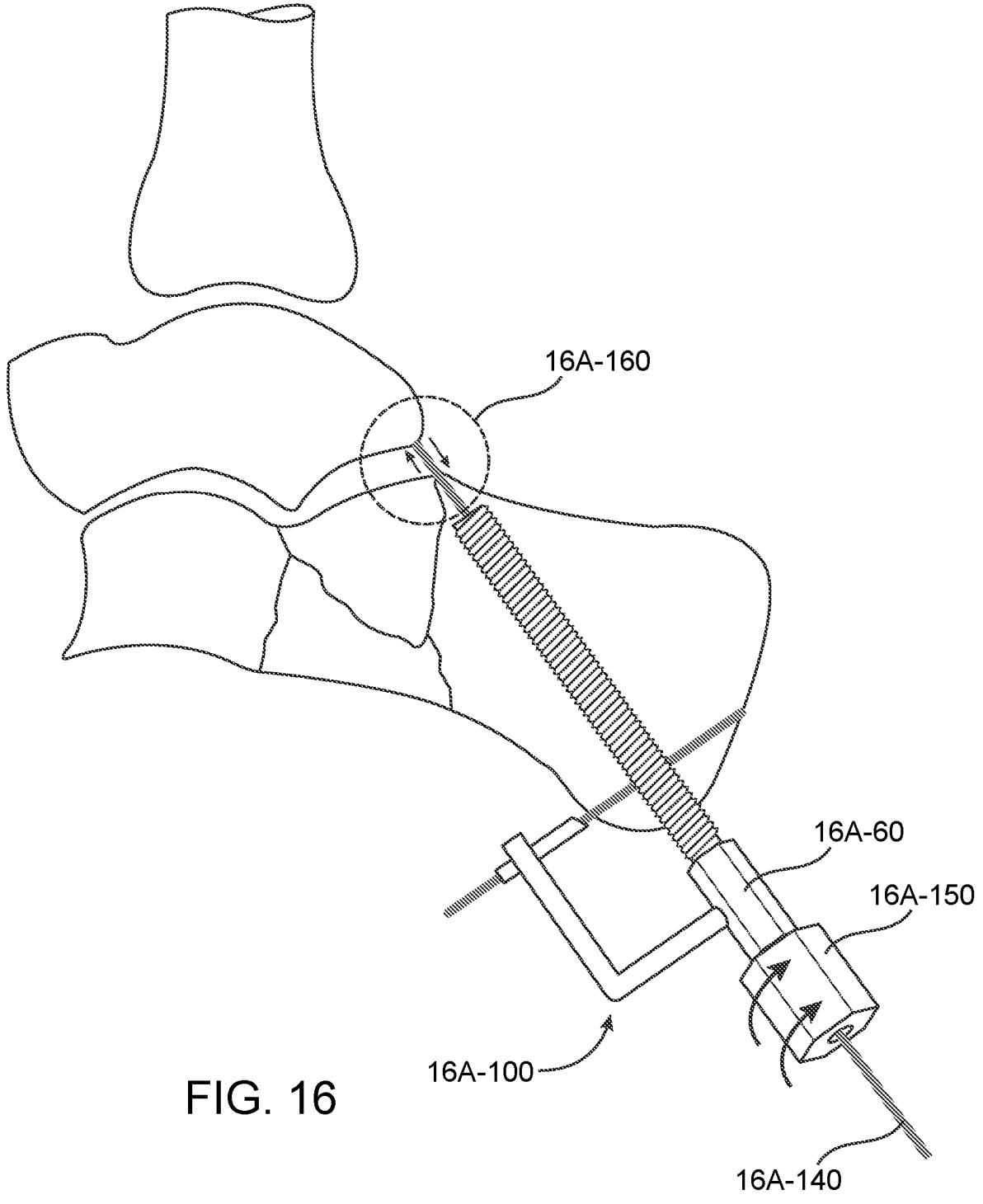
FIG. 16 depicts the distraction capability of an embodiment of the reduction tool.

FIG. 16 depicts the distraction capability of an embodiment of the reduction tool (16A-100). The coupling of the distraction bolt/nut, 16A-150, to the outrigger, 16A-60, provides for the advancement of the distraction wire, 16A-140, with the rotation of the nut/bold 16A-150. The space produced is depicted as distraction at the interface drawn as 16A-160. This distraction induces a potential space to be produced to provide for restoration of the calcaneal anatomy. Of note, the coupling of the distraction bolt/nut, 16A-150, to the outrigger 16A-60, occurs to provide for free rotation of the nut/bolt, 16A-150, allowing for the movement of the threaded distraction wire, 16A-40.

Figure 17:
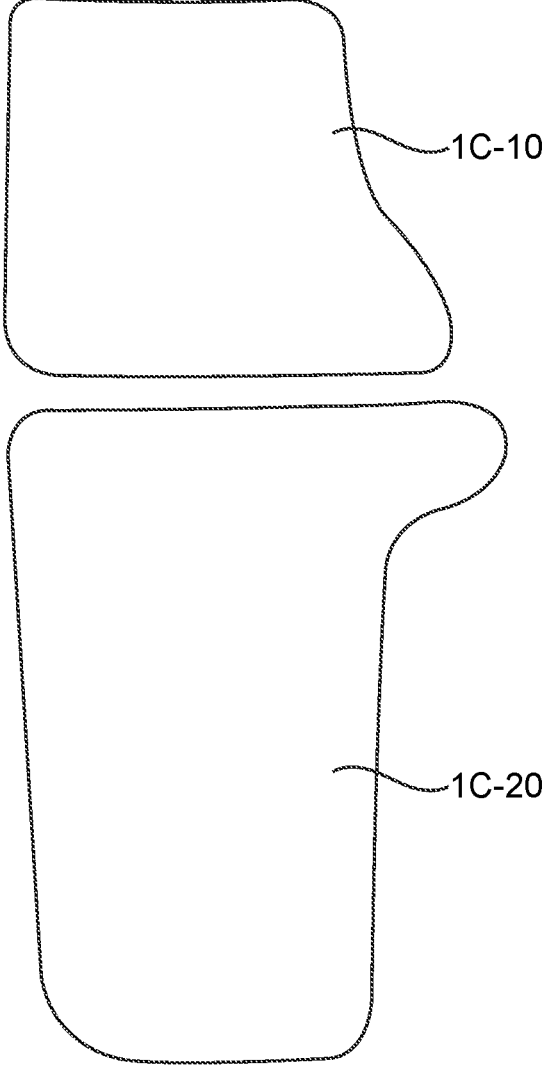
FIG. 17 is a depiction of a calcaneal bone and talus bone in coronal cross-section.

FIG. 17 is a depiction of a calcaneal bone and talus bone in coronal cross-section. Reference numeral 1C-10 indicates the talus, where 1C-20 indicates of the calcaneus. Note, this is only one depiction of the bone via a coronal cross section.

Figure 18:
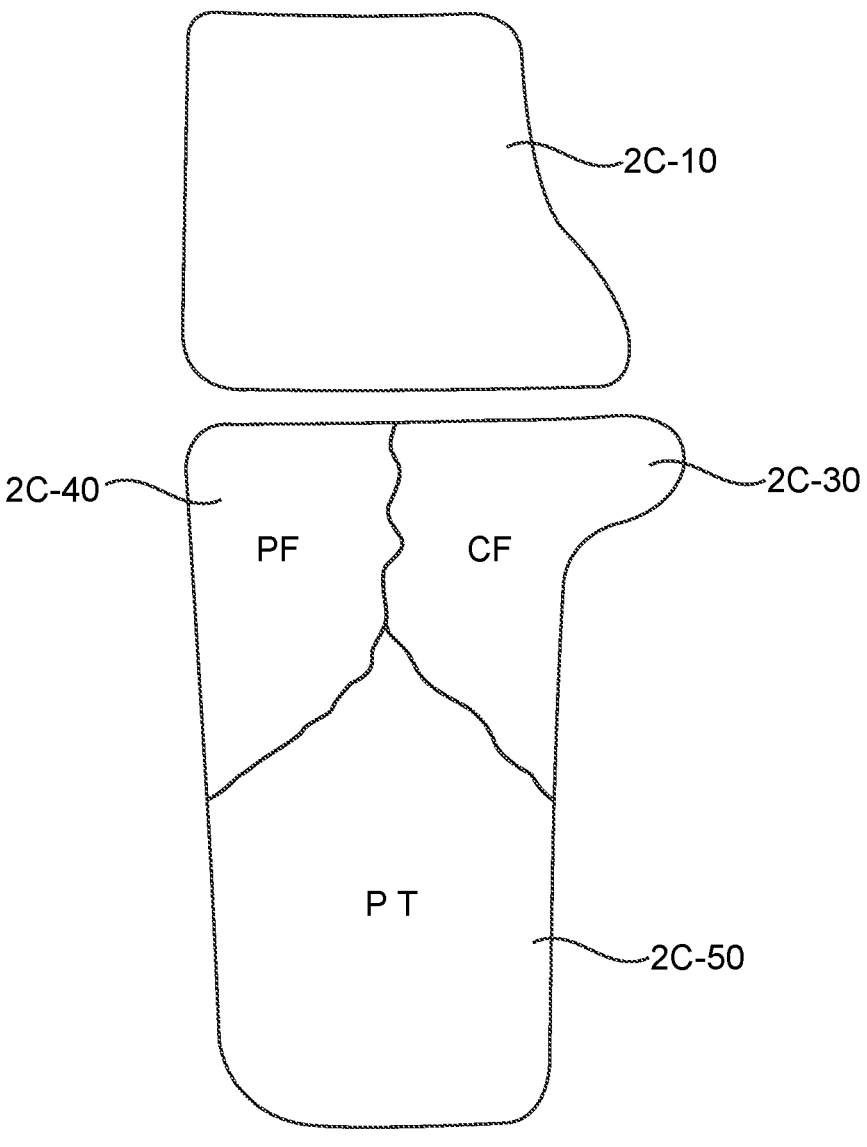
FIG. 18 is a depiction of the same coronal cross section of the talus and calcaneal bone with added features to depict a common fracture pattern through the joint surface.

FIG. 18 depicts of the same coronal cross section of the talus and calcaneal bone with added features to depict a common fracture pattern through the joint surface. The three main components of the fracture are labeled as 2C-30 the constant fragment, 2C-40 the posterior facet fracture fragment, and 2C-50 the posterior tuberosity fracture fragment.

Figure 19:
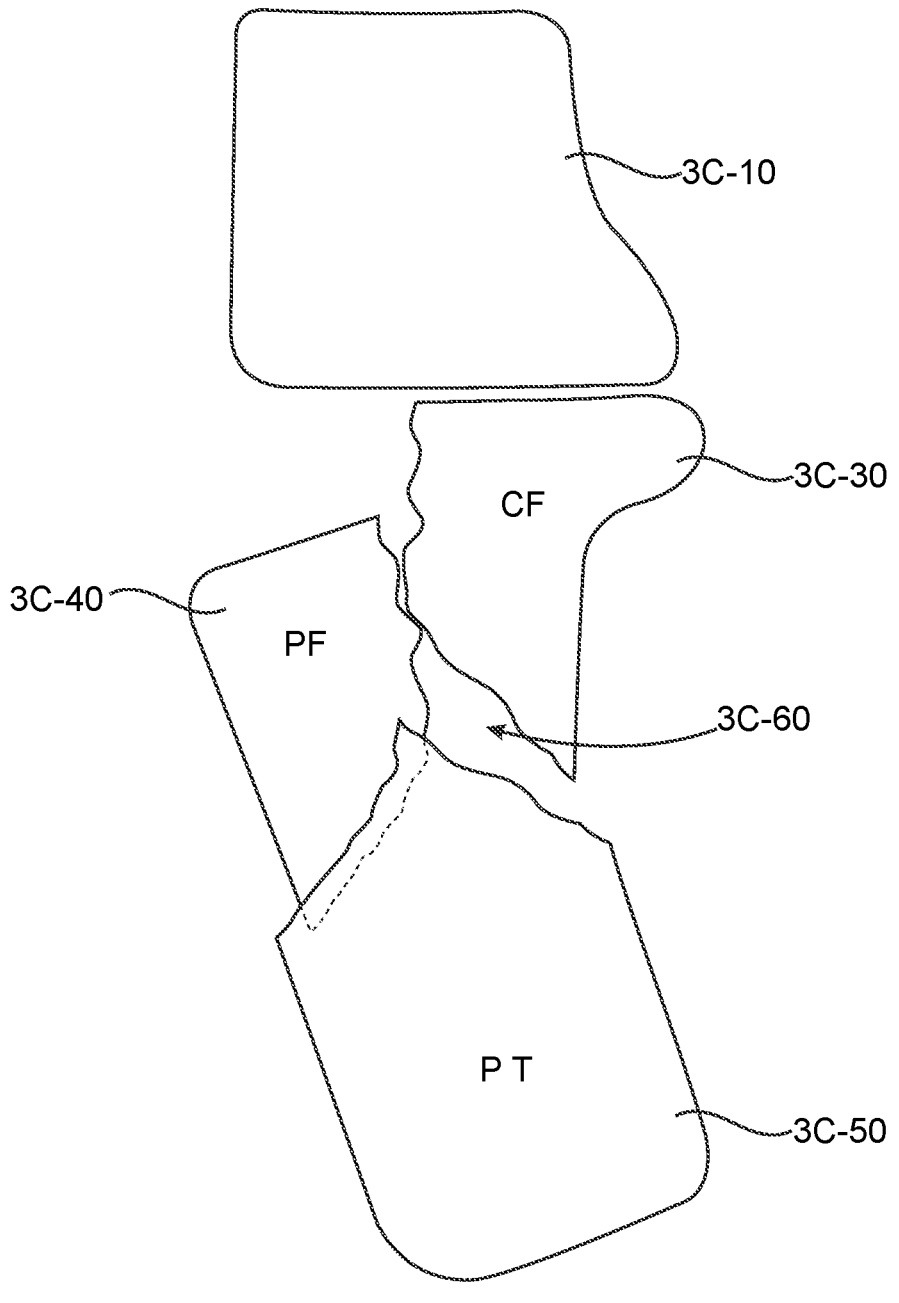
FIG. 19 is a depiction of the same fracture with displacement.

FIG. 19 is a depiction of the same fracture now with displacement. The three main components of the fracture are labeled as 2C-30 the constant fragment, 2C-40 the posterior facet fracture fragment, 3C-50 the posterior tuberosity fracture fragment. Additionally, displacement of the fracture is now depicted with the call out 3C-60.

Figure 20:
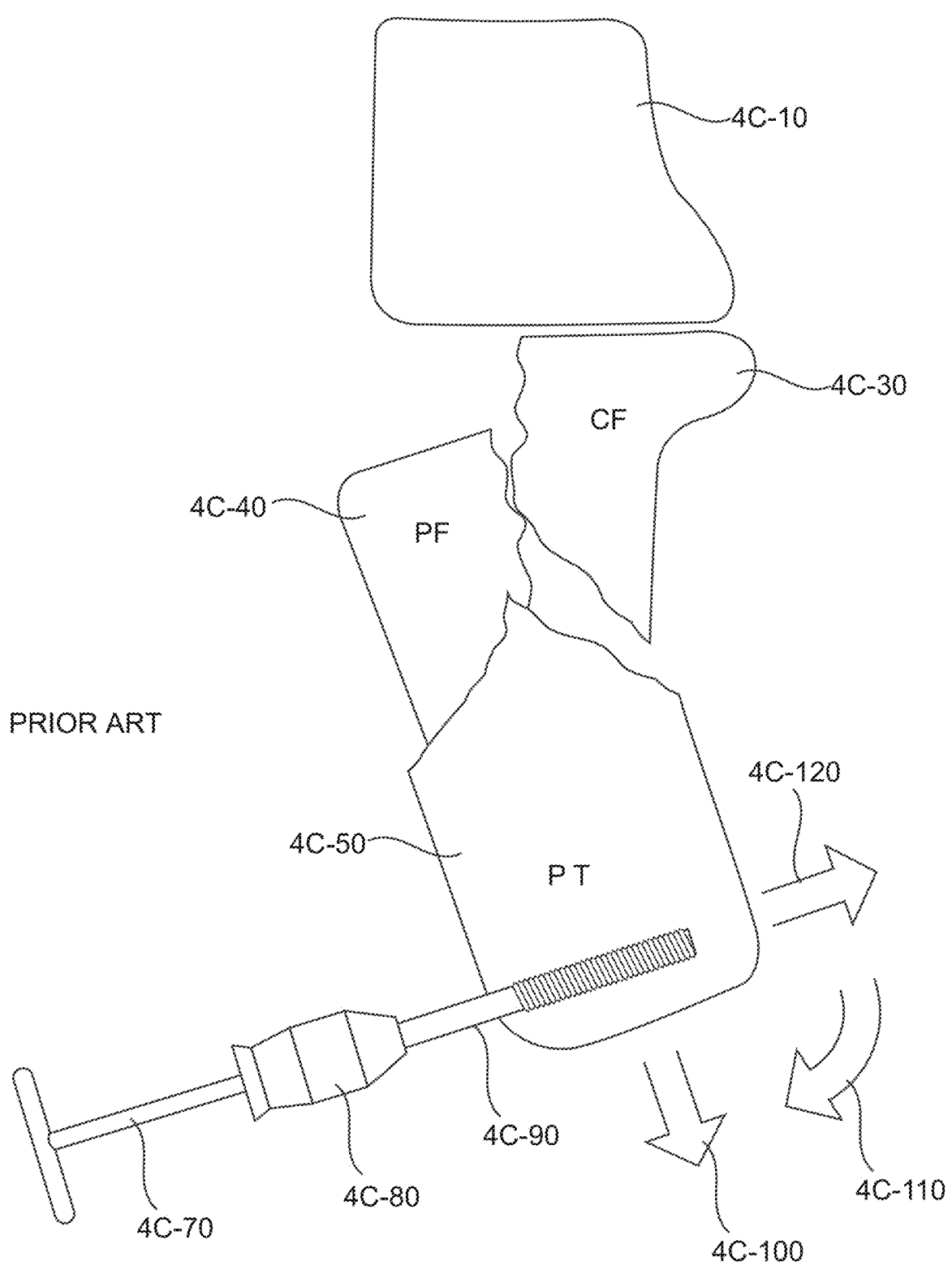
FIG. 20 demonstrates the same displaced fracture with the traditional reduction tools and reduction vectors/maneuvers depicted.

FIG. 20 now demonstrates the same displaced fracture depicted in FIG. 19 with the traditional reduction tools and reduction vectors/maneuvers depicted. The threaded Schantz pin 4C-90 is inserted into the poster tuberosity component of the fracture 4C-50. The Schantz pin is controlled with the use of a T handled chuck shown in combination 4C-70 and 4C-80. With the Schantz pin 4C-90 inserted, reduction vectors/maneuvers are performed to provide for medialization of the posterior tuberosity 4C-50 depicted through arrow vector 4C-120. Additional maneuvers include correction of varus angulation depicted as vector 4C-110 as well as restoration of calcaneal height depicted as vector 4C-100.

Figure 21:
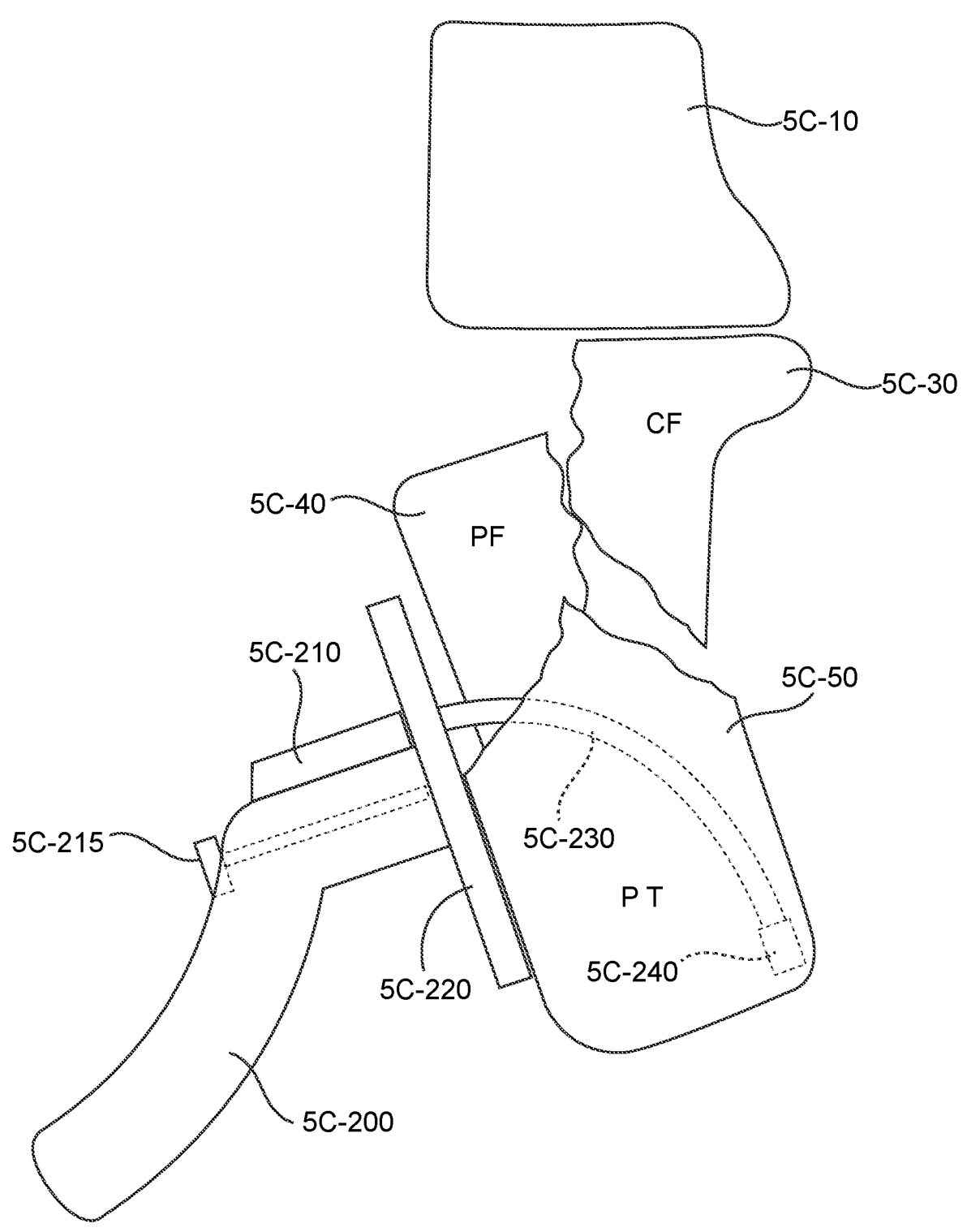
FIG. 21 demonstrates an embodiment of a reduction fixation implant for a calcaneal fracture.

FIG. 21 now demonstrates an embodiment of a novel Reduction fixation implant for a calcaneal fracture. Once again, the talus is shown in corona cross section, 5C-10. Additionally, the displaced calcaneal fracture is depicted with fracture fragments 5C-30, 5-40 and 5C-50. 5C-220 indicates the outline of the lateral wall calcaneal plate. Additional features of this plate include the attached medial column kickstand 5C-230 and the medial column screw capture 5C-240. Attached to the lateral wall plate 5C-220 is the reduction handle/targeter 5C-200. Attachment of the reduction handle/targeter to the plate occurs with the use of registration and an anchor bolt 5C-215, in this embodiment. Finally, the superior reduction wire guide of this embodiment is depicted as 5C-210 attaching to the superior portion of the Reduction handle/targeter 5C-200.

Figure 22:
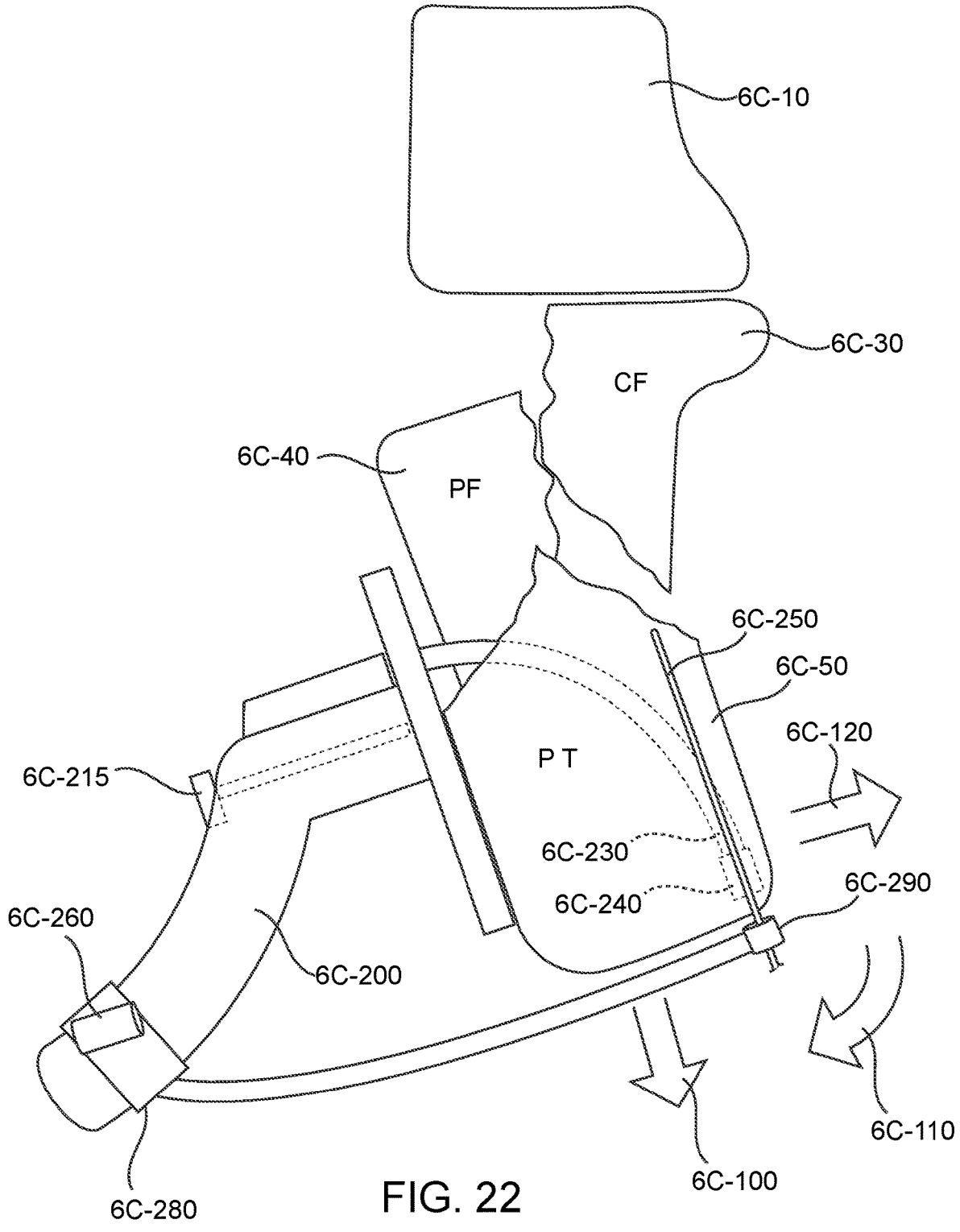
FIG. 22 demonstrates an embodiment of the assembled reduction handle/targeter.

FIG. 22 now demonstrates an embodiment of the assembled reduction handle/targeter noting added component 6C-280, medial column and posterior tuberosity wire targeter placed over assembled reduction handle/targeter 6C-200. Posterior tuberosity wire targeter 6C-280 now can accept medial column reduction wire 6C-250 through wire targeting portal 6C-290 and medial column screw capture 6C-240, located at the terminal end of the medial column kickstand 6C-230. With the medial column reduction wire 6C-250 now inserted through medial column wire targeting portal 6C-290, reduction maneuvers can be performed to restore calcaneal anatomy. Reduction vectors/maneuvers are performed to provide for medialization of the posterior tuberosity 6C-50 depicted through arrow vector 6-120. Additional maneuvers include correction of varus angulation depicted as vector 6C-110 as well as restoration of calcaneal height depicted as vector 6C-100.

Figure 23:
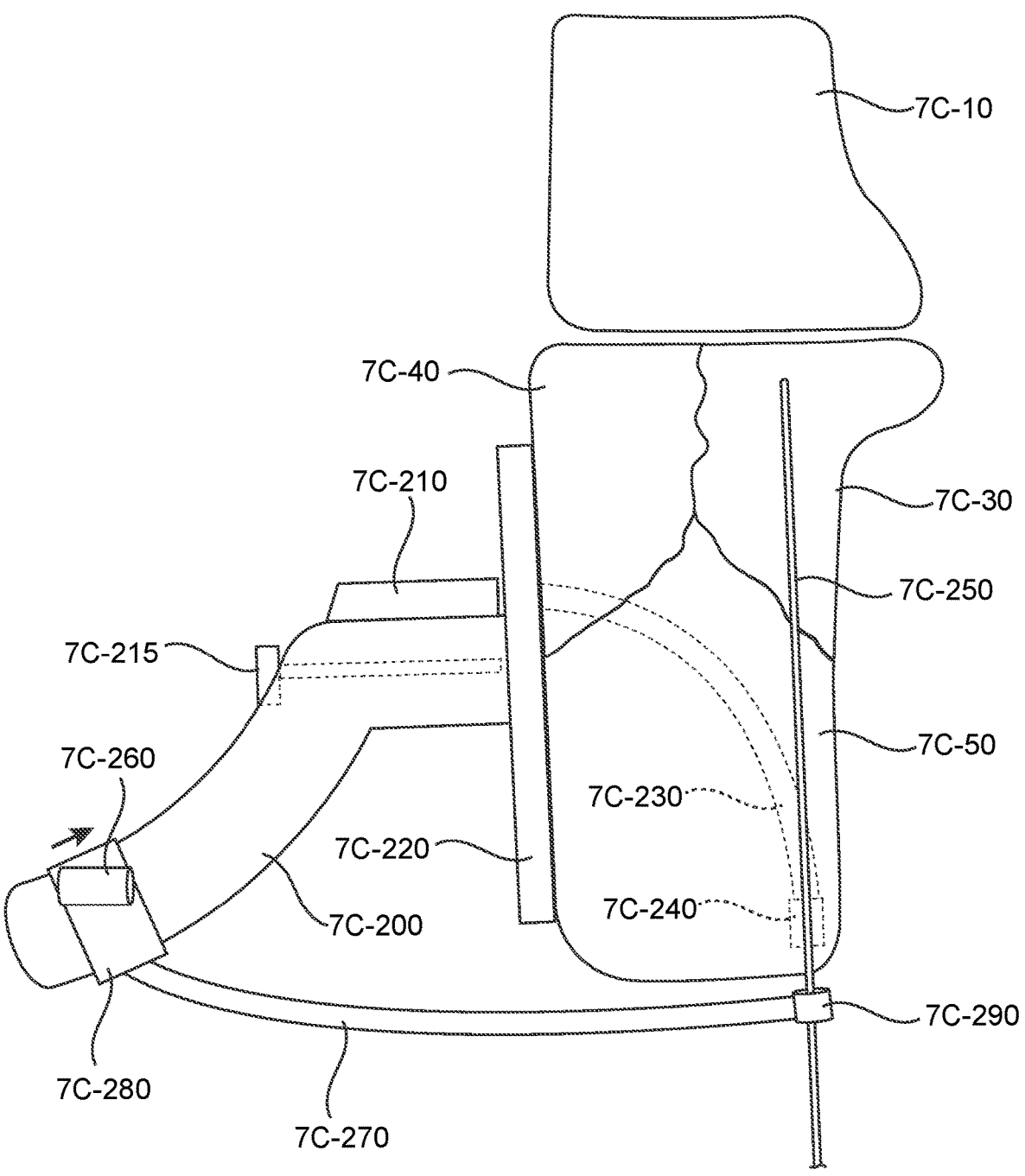
FIG. 23 demonstrates the reduced calcaneal fracture with anatomically reoriented fracture fragments.

FIG. 23 now demonstrates the reduced calcaneal fracture with anatomically reoriented fracture fragments 7C-30, 7C-40 and 7C-50, utilizing embodiments. The medial column reduction wire 7C-250 is now advanced into the constant fragment-portion of the fracture 7C-30 to maintain the fracture reduction and resist varus angulation.

Figure 24:
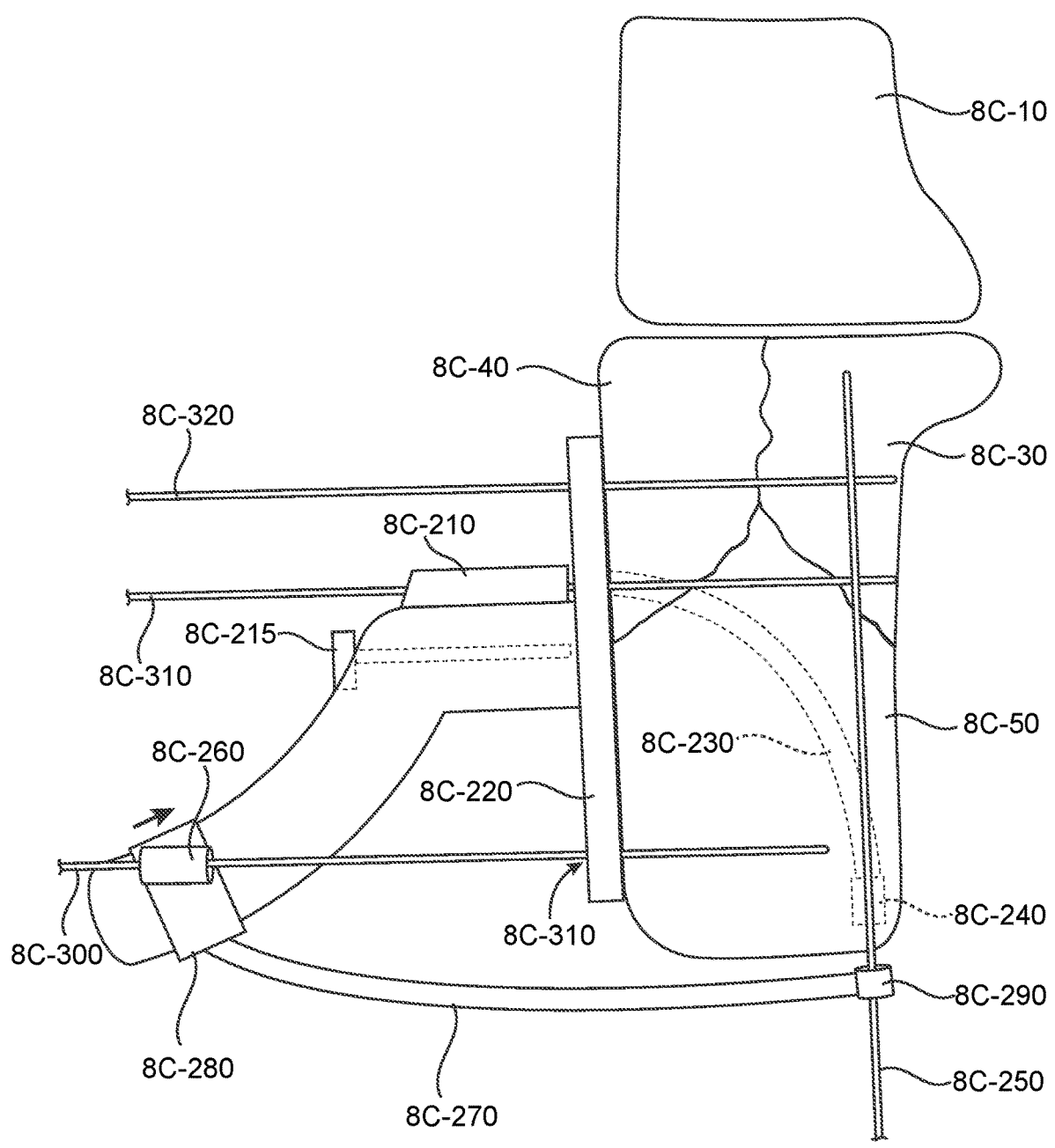
FIG. 24 demonstrates the reduced calcaneal fracture with anatomically reoriented fracture fragments.

FIG. 24 demonstrates the reduced calcaneal fracture with anatomically reoriented fracture fragments 8C-30, 8C-40 and 8C-50, associated with embodiments. The reduction between fracture fragment 8C-30 and fracture fragment 8C-50 is once again maintained through the medial column reduction wire 8C-250. The anatomically reduced fracture is additionally secured with multiple reduction wires, in this depicted embodiment. Starting at the superior border of the lateral wall calcaneal plate 8C-220 is the articular reduction wire 8C-320 that is placed through the lateral wall calcaneal plate 8C-220. Inferior to the articular reduction wire 8C-320 is the crucial angle reduction wire 8C-310 inserted through both the superior reduction wire guide 8C-210 and the lateral wall calcaneal plate 8C-220, in this embodiment. Finally, the inferior posterior tuberosity reduction wire 8C-300 is inserted through the posterior tuberosity reduction wire guide 8C-260 and the lateral while calcaneal plate 8C-220 at interface 8C-310.

Figure 25:
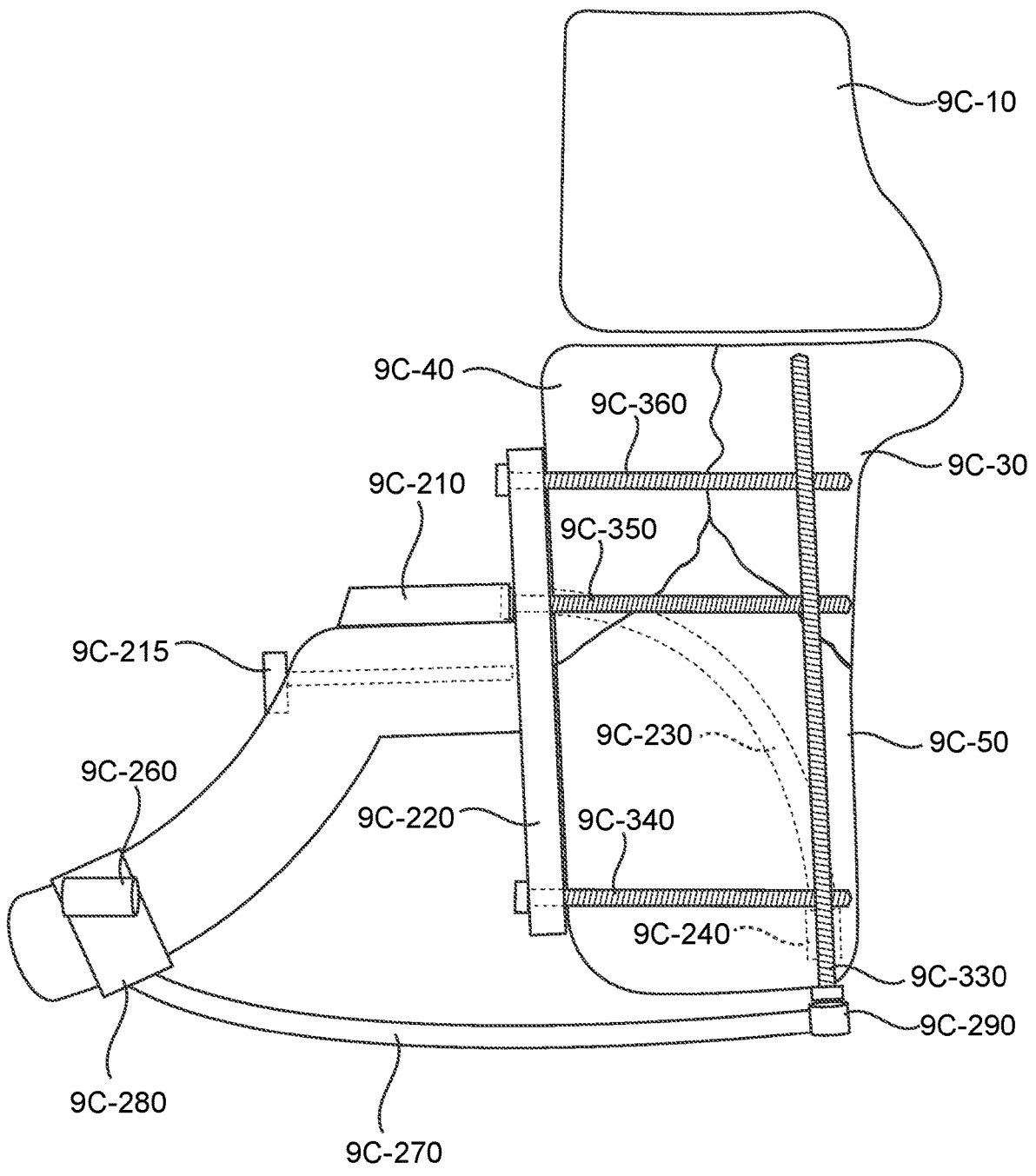
FIG. 25 demonstrates the exchange of fixation screws for previously inserted reduction wires, in the current embodiment.

FIG. 25 now demonstrates the exchange of fixation screws for previously inserted reduction wires, in the current embodiment. These screws can either be solid core or cannulated. Medial column reduction screw 9C-330 has been placed through medial column wire targeting portal 9C-290 and medial column screw capture 9C-240. Articular reduction screw 9C-360 has been placed through the lateral wall calcaneal plate 9C-220 to secure the articular reduction between fracture fragments 9C-40 and 9C-30. Crucial angle reduction screw in 9C dash 350 has been inserted through superior reduction wire guide 9C-210 and lateral wall calcaneal plate 9C-220. This screw affords the opportunity to capture and maintain alignment through all three fracture fragments 9C-30, 9C-40 and 9C-50. Final screw placement his depicted as posterior tuberosity screw 9C-340 inserted through the posterior tuberosity reduction wire guide 9C-260 and the lateral while calcaneal plate 9C-220.

Figure 26:
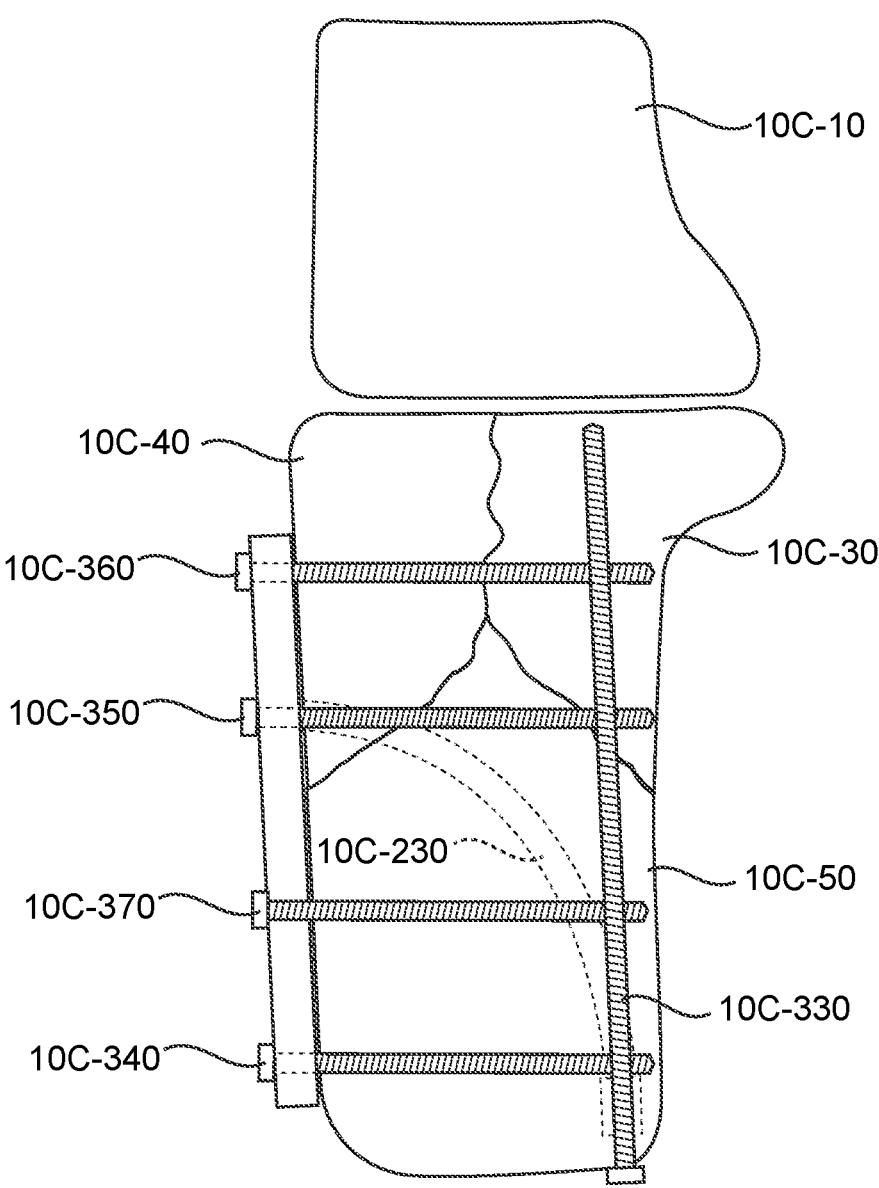
FIG. 26 demonstrates final reduction of the fracture fragments and assembly of the plate screw construct.

FIG. 26 demonstrates a final reduction of the fracture fragments and final assembly of the plate screw construct associated with this embodiment. Fracture fragments 10C-30, 10C-40 and 10C-50 are anatomically reoriented below talus 10C-10. The plate 10C-220 and the adjoining medial column kickstand 10C-230 are secured to the fracture with the use of the following screws: Medial column reduction screw 10C-330, Articular reduction screw 10C-360, Crucial angle reduction screw 10C-350, Posterior tuberosity reduction screw 10C-340, and optional supplemental fixation screw 10C-370.

The above description has particularly shown and described example embodiments. However, it will be understood by those skilled in the art that various changes in form and details may be made therein without departing from the legal scope of this patent as encompassed by the appended claims.

The invention claimed is:

1. A cannulated Schantz pin for acting on a bone fragment comprising:
 a threaded portion configured for interfacing with the bone fragment;
 a canulated center portion for accepting a wire;
 a coupling interface portion for:
  insertion and extraction of the cannulated Schantz pin;
  interfacing to a canulated manipulation handle, such that the cannulated Shantz pin is at least partially insertable into, and subsequently extractable from, the cannulated manipulation handle;
  wherein the manipulation handle, when interfaced to the cannulated Shantz pin, is further configured for adjusting a position of the bone fragment relative to one or more other bone fragments prior to the insertion of the wire through the cannulated Shantz pin and into the bone fragment;
  wherein the manipulation handle further includes an interface to an aligning structure configured to accept an anchoring wire configured for providing mechanical support between the cannulated Shantz pin and the bone fragment; and

wherein the cannulated Schantz pin is further config-
ured for removal from the bone fragment following
the insertion of the wire into the one or more other
bones or other bone fragments while leavening the
wire in place and allowing the wire to retain align-
ment during an exchange of the cannulated Shantz
pin with a cannulated screw that also fits over the
wire;
wherein the coupling interface portion is further con-
figured to mechanically interact with a distraction
bolt and/or a compression bolt via the manipulation
handle; and
wherein the wire further includes a threaded portion to
interface with the distraction bolt and/or compres-
sion bolt so as to apply force to the wire relative to
the Schantz pin.

2. The cannulated Schantz pin of claim 1 wherein the
distraction bolt and/or compression bolt is further usable to
adjust a position of the wire relative to the pin so as to
shorten or lengthen a portion of the wire extending beyond
the pin in situ.

3. The cannulated Schantz pin of claim 1 wherein a distal
end of the wire interfaces with at least one of the one or more other bones or other bone fragments to adjust a relative
position of the Schantz pin.

4. The cannulated Schantz pin of claim 1 wherein the
configuration of the cannulated Schantz pin allowing for the
insertion of the wire into the one or more other bones or bone
fragments further allows for the wire to be inserted into at
least one of the other bones or other bone fragments, so as
to retain alignment of the one or more other bones or bone
fragments with the at least one of the other bone or bone
fragments following removal of the Shantz pin so as to
further allow the wire to retain alignment during the
exchange of the Shantz pin with the cannulated screw.

5. The cannulated Schantz pin of claim 1 wherein the
cannulated manipulation handle further includes a first
mechanical coupling for interfacing with the pin, and a
second mechanical coupling for interfacing with the distrac-
tion bolt and/or compression bolt.

6. The cannulated Schantz pin of claim 1 wherein the
cannulated manipulation handle is further configured to
accept the anchoring wire so as to secure mechanical align-
ment of the pin and the bone fragment relative to one or
more other bones or other bone fragments.

* * * * *